United States Patent [19]

Noguchi

[11] Patent Number: 4,924,856
[45] Date of Patent: May 15, 1990

[54] ENDOSCOPE LIGHT SOURCE APPARATUS

[75] Inventor: Toshiaki Noguchi, Tachikawa, Japan

[73] Assignee: Olympus Optical Co., Ltd., Tokyo, Japan

[21] Appl. No.: 333,653

[22] Filed: Apr. 5, 1989

[30] Foreign Application Priority Data

Apr. 8, 1988 [JP] Japan .................................. 63-87522
Mar. 8, 1989 [JP] Japan ................................. 63-057262

[51] Int. Cl.⁵ .............................................. A61B 1/04
[52] U.S. Cl. .......................................... 128/6; 358/98
[58] Field of Search ........................ 128/4, 6; 358/98

[56]  References Cited
U.S. PATENT DOCUMENTS

| 4,369,767 | 1/1983 | Shishido | 128/6 |
| 4,710,807 | 12/1987 | Chikama | 128/6 X |
| 4,713,683 | 12/1987 | Fujimori et al. | 358/98 X |
| 4,742,277 | 5/1988 | Shibuya et al. | 315/176 |
| 4,800,424 | 1/1989 | Noguchi | 358/98 |

FOREIGN PATENT DOCUMENTS 60-76888 5/1985 Japan .
60-243625 12/1985 Japan .
61-82731 4/1986 Japan .

Primary Examiner—William H. Grieb
Attorney, Agent, or Firm—Armstrong, Nikaido, Marmelstein, Kubovcik & Murray

[57] ABSTRACT

This endoscope light source apparatus can feed an illuminating light to an endoscope requiring a white color light as an illuminating light and to an endoscope having a field sequential type imaging apparatus and requiring as an illuminating light a field sequential light sequentially switched to lights in different wavelength ranges and comprises a light source emitting a white color light, a converting apparatus interposed in the light path of the light emitted from the light source at least at the time of outputting a field sequential light and converting the white color light emitted from the light source to a field sequential light, a selecting apparatus selecting the kind of the emitted light from among a white color light and field sequential light and a light amount controlling apparatus whereby, when a field sequential light is selected by the selecting apparatus, during the exposure period of the field sequential type imaging apparatus, the light amount of the light source can be increased to be larger than outside the exposure period. Also, the endoscope light source apparatus comprises a light source, converting apparatus, selecting apparatus and light amount controlling apparatus whereby, when a field sequential light is selected by the selecting apparatus, the light amount of the light source can be increased to be larger than at the time of outputting a white color light.

20 Claims, 19 Drawing Sheets (a) LAMP CURRENT LIGHTING TIME 18A

0A (b) SCOPE TIP EMITTED LIGHT AMOUNT (a) LAMP CURRENT LIGHTING TIME 18A

0A (b) SCOPE TIP EMITTED LIGHT AMOUNT

R  G  B (a) LAMP CURRENT LIGHTING TIME 18A

0A (b) SCOPE TIP EMITTED LIGHT AMOUNT (a) LAMP CURRENT LIGHT INCREASING TIME 25A 10A
0A (b) SCOPE TIP EMITTED LIGHT AMOUNT 1.5
0

R  G  B

ENDOSCOPE LIGHT SOURCE APPARATUS

BACKGROUND OF THE INVENTION

1. Field of the Invention:

This invention relates to an endoscope light source apparatus which can output a white color light and a field sequential light.

2. Related Art Statement:

Recently, there is extensively used an endoscope (called also a scope or fiber scope) whereby organs within a body cavity can be observed by inserting an elongate insertable part through the body cavity and, as required, various therapeutic treatments can be made by inserting treating instruments through a treating instrument channel.

Various electronic scopes using such solid state imaging device as a charge coupled device (CCD) are also suggested. Such electronic scope has advantages that the resolution is higher than in a fiber scope, it is easier to record and reproduce picture images and such picture image processing as the enlargement of picture images or the comparison of two picture images is easier.

Among systems of imaging color picture images of the above mentioned electronic scope, there are such field sequential type sequentially switching an illuminating light to R (red), G (green) and B (blue) as is shown, for example, in the publication of Japanese patent application Laid Open No. 82731/1986 and such simultaneous type wherein a filter array in which color filters respectively transmitting such color lights as of R, G and B are arranged in the form of a mosaic is provided on the front surface of a solid state imaging device as is shown, for example, in the publication of Japanese patent application Laid Open No. 76888/1985. The field sequential type has an advantage that the number of pixels can be made lower than in the simultaneous type. On the other hand, the simultaneous type has an advantage that no color smear will be produced.

The above mentioned electronic scope is made in many kinds by its using objects. For example, an insertable part of an outside diameter of about 10 mm. is used for an upper or lower digestive organ. On the other hand, for example, an insertable part of an outside diameter of about 5 mm. is usually required for a bronchus. It is physically and operatively unreasonable to use the same kind of imaging device and the same kind of imaging system for various electronic scopes of outside diameters of the insertable parts thus varying in a wide range. That is to say, for example, in order to realize an electronic scope for a bronchus (fine diameter), an imaging device of few pixels can not help being used.

Thus, in the case of few pixels, in order to prevent the reduction of the resolution, a field sequential type color imaging system whereby the object is illuminated in a field sequential system with lights of respective wavelengths of R, G and B and is imaged field-sequentially under the illumination and these images are combined and color-displayed is more advantageous than a simultaneous type imaging system using a color mosaic filter.

On the other hand, for the outside diameter of about 10 mm., it is advantageous in order to improve the picture quality to increase the number of pixels and to make the imaging system a simultaneous type.

Now, the above mentioned fiber scope or electronic scope is used generally as connected with a light source apparatus feeding an illuminating light adapted to each scope.

The illuminating method is different in the above mentioned fiber scope, field sequential type electronic scope and simultaneous type electronic scope. That is to say, a white color light required in the fiber scope and simultaneous type electronic scope and a light sequentially switched to R, G and B is required in the field sequential type electronic scope. However, the conventional light source apparatus can output an illuminating light corresponding to only one of the field sequential type electronic scope, simultaneous type electronic scope and fiber scope. Therefore, the user must prepare respectively different light source apparatus and make different operations depending on the kind of the scope and the economy and efficiency have been low.

By the way, the publication of Japanese patent application Laid Open No. 243625/1985 discloses a connecting system whereby a fiber scope provided with an image transmitting optical fiber bundle is connected to a control apparatus of an electronic scope provided with a field sequential type light source apparatus so that the image may be observed on such displaying picture surface as of a monitor television. However, with this system, a simultaneous type electronic scope can not be used and the image can not be observed with a naked eye by using a fiber scope.

Therefore, the present Applicant has suggested, for example, in the previously filed U.S. patent application Ser. Nos. 150,255 and 155,396 an endoscope light source apparatus which can output a white color light and field sequential light.

Now, a halogen lamp or xenon lamp is used for the illuminating means of such light source apparatus which can output a white color light and field sequential light. In such case, the emitted light of the lamp will be fed as a continuous light. However, in case a field sequential type electronic scope is used, the light emitted from the tip of this electronic scope will be intercepted during the CCD charge transferring period by the rotation of a color converting filter provided between the lamp within the light source apparatus and the light guide entrance end of the electronic scope and therefore approximately more than half the light will not be emitted. On the other hand, in case a fiber scope or a simultaneous type electronic scope is used, the above mentioned color converting filter will not be required. Therefore, the light emitted from the tip of the scope in this case will effectively use the light emitted from the lamp.

Thus, in case the fiber scope and simultaneous type electronic scope are used, the light amount of the light emitted from the tip of the scope will effectively use the emitted light of the lamp and therefore will be bright enough for the observation. On the other hand, in case the field sequential type electronic scope is used, during the CCD charge transferring period, the emitted light from the lamp will be intercepted by the light intercepting parts of the color converting filter, the light emitted from the lamp will not be effectively utilized and the total light amount emitted from the scope tip will greatly reduce. That is to say, there are disadvantages that, in case a field sequential type electronic scope is used, the light amount emitted from the scope tip will be less than in the case of a fiber scope or simultaneous type electronic scope, will be short and will not be enough to be fed to the observed object and the observing capacity will reduce.

OBJECTS AND SUMMARY OF THE INVENTION

An object of the present invention is to provide an endoscope light source apparatus which can output a white color light and field sequential light and can feed a sufficient light amount even at the time of outputting a field sequential light.

Another object of the present invention is to provide an endoscope light source apparatus which can output a white color light and field sequential light and can effectively utilize the light emitted from the light source at the time of outputting the field sequential light.

The endoscope light source apparatus can feed an illuminating light to an endoscope requiring a white color light as an illuminating light and an endoscope provided with a field sequential type imaging means and requiring as an illuminating light a field sequential light switched sequentially to lights in different wavelength ranges and comprises a light source emitting a white color light, a converting means interposed in the light path of the light emitted from the above mentioned light source at least at the time of outputting a field sequential light and converting the white color light emitted from the above mentioned light source to a field sequential light, a selecting means selecting the kind of the output light from among a white color light and field sequential light and a light amount controlling means which can increase the light amount of the above mentioned light source to be larger than in the other periods than the exposure period during the exposure period of the imaging means of the above mentioned field sequential type when a field sequential light is selected by the above mentioned selecting means.

Also, the endoscope light source apparatus comprises the above mentioned light source, the above mentioned converting means, the above mentioned selecting means and a light amount controlling means which can increase the light amount of the above mentioned light source to be larger than at the time of outputting a white light when a field sequential light is selected by the above mentioned selecting means.

The other features and advantages of the present invention will become apparent enough with the following explanation.

BRIEF DESCRIPTION OF THE DRAWINGS

FIG. 1 is an explanatory view showing the whole of an endoscope system.

FIG. 2 is an explanatory view showing a fiber scope.

FIG. 3 is an explanatory view showing an externally fitted field sequential type television camera.

FIG. 4 is an explanatory view showing an externally fitted simultaneous type television camera.

FIG. 5 is an explanatory view showing a field sequential type electronic scope.

FIG. 6 is an explanatory view showing a simultaneous type electronic scope.

FIG. 7 is a block diagram showing the formation of a video processor.

FIG. 8 is a block diagram showing the formation of a camera control unit.

FIG. 9 is a block diagram showing the formation of a field sequential type process circuit.

FIG. 10 is a block diagram showing the formation of a simultaneous type process circuit.

FIG. 11 is a perspective view showing a filter moving means of a light source apparatus.

FIG. 12 is an elevation of a color converting filter.

FIG. 13 is an explanatory view showing a lamp current and scope tip emitted light amount at the time of outputting a white color light in a light source apparatus of a comparative example.

FIG. 14 is an explanatory view showing a lamp current and scope tip emitted light amount at the time of outputting a field sequential light in a light source apparatus of a comparative example.

FIG. 15 is an explanatory view showing a lamp current and scope tip emitted light amount at the time of outputting a white color light in a light source apparatus of this embodiment.

FIG. 16 is an explanatory view showing a lamp current and scope tip emitted light amount at the time of outputting a field sequential light in a light source apparatus of this embodiment.

FIG. 17 is a timing chart showing the operation of this embodiment.

FIG. 20 is an explanatory view showing a light source apparatus.

FIG. 21 is a view as seen in the direction indicated by the arrow D in FIG. 20 and showing the stopping position of a color converting filter at the time of outputting a white color light.

FIG. 22 is a block diagram showing the formation of a field sequential type process circuit.

FIG. 24 is an explanatory view showing a light source apparatus.

FIG. 25 is a timing chart showing the operation of another embodiment for the comparison with that of this embodiment.

FIG. 26 is a timing chart showing the operation of this embodiment.

FIG. 27 is an elevation of a color converting filter.

FIG. 28 is a side view of a color converting filter.

FIG. 29 is a timing chart showing the operation of this embodiment.

DETAILED DESCRIPTION OF PREFERRED EMBODIMENTS

The first embodiment of the present invention is shown in FIGS. 1 to 17.

Figure 1:
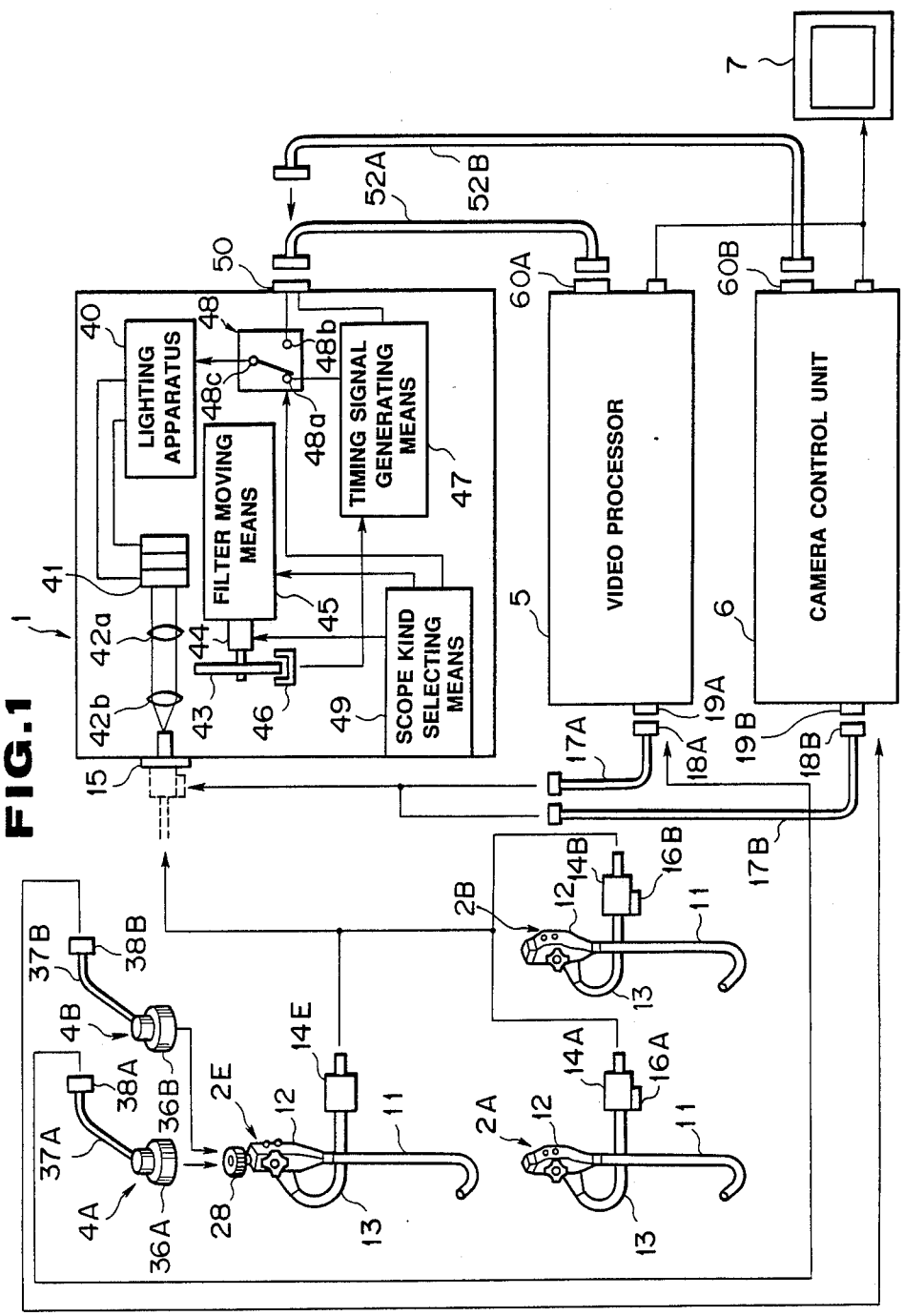
FIGS. 1 to 17 relate to the first embodiment of the present invention.

As shown in FIG. 1, an endoscope system comprises an endoscope light source apparatus 1, a fiber scope 2E whereby a naked eye observation is possible as an endoscope (mentioned as a scope hereinafter) connected to this light source apparatus, a field sequential type electronic scope 2A having a field sequential type imaging means, a simultaneous type electronic scope 2B having a simultaneous type imaging means, an externally fitted field sequential type television camera 4A as an externally fitted television camera removably connected to the eyepiece part of the above mentioned fiber scope 2E to display a picture image in a monitor, an externally fitted simultaneous type television camera 4B, a video processor 5 connected with the above mentioned field sequential type electronic scope 2A or externally fitted field sequential type television camera 4A and processing signals therefor, a camera control unit 6 connected with the above mentioned simultaneous type electronic scope 2B or externally fitted simultaneous type television camera 4B and processing signals therefor and a television monitor 7 connected to the above mentioned video processor 5 and camera control unit 6.

Each of the above mentioned scopes 2E, 2A and 2B is provided with an elongate and, for example, flexible insertable part 11 to the rear end of which a thick operating part 12 is connected. A flexible universal cord 13 is extended sidewise from the above mentioned operating part 12 and is provided at the tip with a light source connector 14E, 14A or 14B which is to be connected to a light source connector receptacle 15 of the above mentioned light source apparatus 1.

In the above mentioned field sequential type electronic scope 2A and simultaneous type electronic scope 2B, electric connector receptacles 16A and 16B are provided respectively on the sides of the above mentioned light source connectors 14A and 14B and are to be connected respectively with signal cords 17A and 17B at the ends. Electric connectors 18A and 18B provided respectively at the other ends of these signal cords 17A and 17B are to be connected respectively to an electric connector receptacle 19A of the above mentioned video processor 5 and an electric connector receptacle 19B of the above mentioned camera control unit 6.

The above mentioned light source apparatus 1, video processor 5 and camera control unit 6 are provided respectively with corresponding electric connector receptacles 50, 60A and 60B. The above mentioned electric connector receptacles 50 and 60A are to be connected with each other through a rear cable 52A and the above mentioned electric connector receptacles 50 and 60B are to be connected with each other through a rear cable 52B. Through the above mentioned rear cables 52A and 52B, signals of freezing and releasing switches and various timing signals are to be transmitted and received between the light source apparatus 1 and video processor 5 and between the light source apparatus and camera control unit 6.

Figure 2:
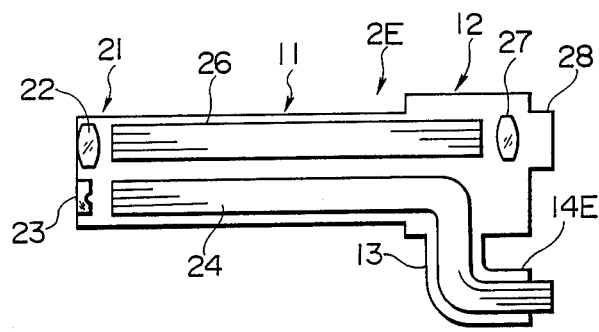
Figure 5:
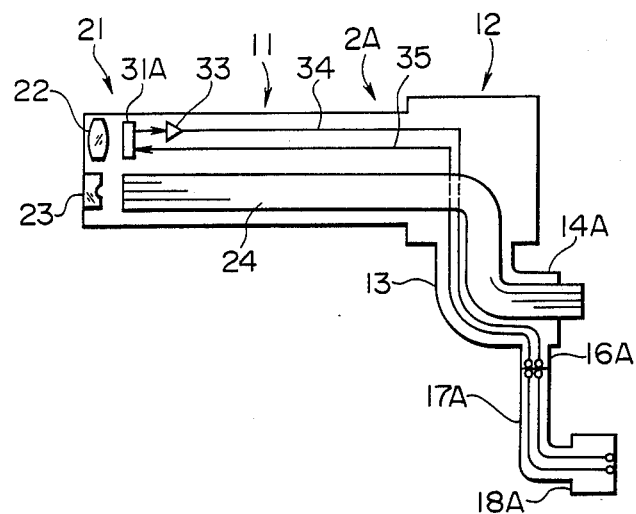
Figure 6:
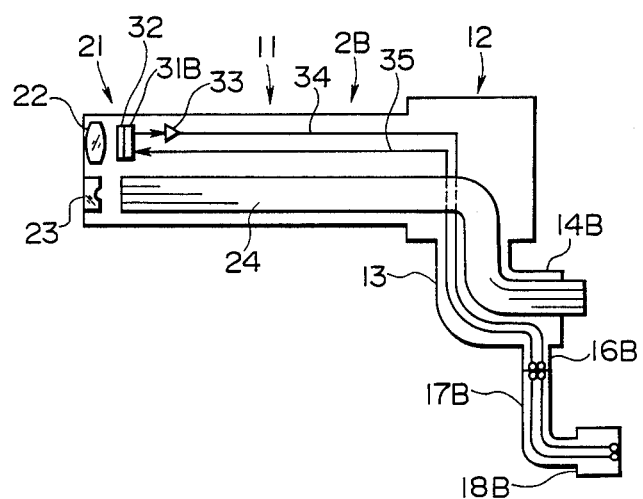

The interiors of the above mentioned scopes 2E, 2A and 2B are so formed as are shown respectively in FIGS. 2, 5 and 6.

In each of the scopes 2E, 2A and 2B, an objective lens system 22 and light distributing lens 23 are arranged in a tip part 21 of an insertable part 11. A light guide 24 transmitting an illuminating light is provided on the rear end side of the above mentioned light distributing lens 23, is inserted through the above mentioned insertable part 11 and universal cord 3 and is connected to the above mentioned light source connector 14E, 14A or 14B. When this light source connector 14E, 14A or 14B is connected to the light source connector receptacle 15 of the light source apparatus 1, an illuminating light adapted to each scope will be fed to the above mentioned light guide 24 at the entrance end from this light source apparatus 1. This illuminating light is led to the tip part 21 by the above mentioned light guide 24, is emitted from the exit end of this light guide 24 and is radiated to an object through the light distributing lens 23.

As shown in FIG. 2, in the fiber scope 2E, the tip surface of the image guide 26 inserted through the insertable part 11 is arranged in the image forming position of the above mentioned objective lens system 22. An eyepiece part 28 having an eyepiece lens 27 opposed to the rear end surface of the above mentioned image guide 26 is provided at the rear end of the operating part 12. The object image formed on the tip surface of the image guide 26 by the above mentioned objective lens system 22 is transmitted to the above mentioned eyepiece part 28 side by the above mentioned image guide 26 and is observed through the eyepiece lens 27 from this eyepiece part 28. On the other hand, as shown in FIGS. 5 and 6, in the field sequential type electronic scope 2A or simultaneous type electronic scope 2B, such solid state imaging device as, for example, a CCD 31A or 31B as an imaging means is arranged in the image forming position of the above mentioned objective lens system 22. By the way, a color filter array in which color filters transmitting respectively such color lights as of red (R), green (G) and blue (B) are arranged in the form of a mosaic is provided on the front surface of the CCD 31B of the simultaneous type electronic scope 2B.

A signal outputting signal line 34 and driving pulse applying signal line 35 are connected to each of the above mentioned CCD's 31A and 31B through a preamplifier 33. The above mentioned signal lines 34 and 35 are inserted through the above mentioned insertable part 11 and universal cord 13 and are connected to the electric connector receptacles 16A and 16B.

Figure 3:
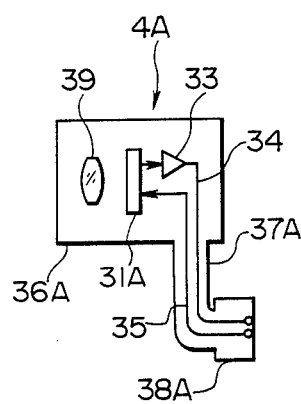
Figure 4:
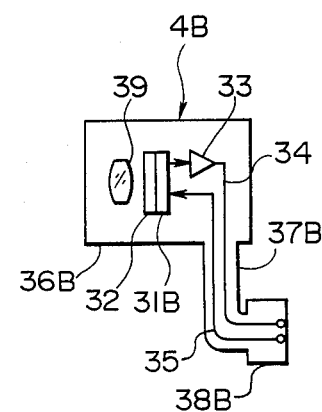

The above mentioned externally fitted field sequential type television camera 4A and externally fitted simultaneous type television camera 4B are formed respectively as shown in FIGS. 3 and 4.

That is to say, the television cameras 4A and 4B comprise respectively camera bodies 36A and 36B to be removably connected to the eyepiece part 28 of the above mentioned fiber scope 2E, signal cords 37A and 37B extended from these bodies 36A and 36B and electric connectors 38A and 38B provided at the tips of these signal cords 37A and 37B. The electric connector 38A of the above mentioned externally fitted field sequential type television camera 4A is to be connected to the electric connector receptacle 19A of the video processor 5. On the other hand, the electric connector 38B of the externally fitted simultaneous type television camera 4B is to be connected to the electric connector receptacle 19B of the camera control unit 6. Within each of the above mentioned camera bodies 36A and 36B, an image forming lens 39 forming the image of the light from the above mentioned eyepiece part 28 is provided and each of the CCD's 31A and 31B is arranged in the image forming position of this image forming lens 39. By the way, a color filter array 32 in which color filters transmitting respectively such color lights as of R, G and B are arranged in the form of a mosaic is provided on the front surface of the CCD 31B of the externally fitted simultaneous type television camera 4B. A signal outputting signal line 34 and driving pulse applying signal line 35 are connected to the above mentioned respective CCD's 31A and 31B through a pre-amplifier 33. The above mentioned signal lines 34 and 35 are inserted through the above mentioned signal cords 37A and 37B and are connected to the electric connectors 38A and 38B.

By the way, a still camera or cine camera not illustrated can be connected to the eyepiece part 28 of the above mentioned fiber scope 2E.

Now, in the case of naked eye observing with a fiber scope 2E, the case of using the externally fitted simultaneous type television camera 4B, still camera or cine camera as connected to the eyepiece part 28 of the fiber scope 2E and the case of using the simultaneous type electronic scope 2B, a white color light will be required as an illuminating light. On the other hand, in the case of using the externally fitted field sequential type television camera 4B as connected to the eyepiece part 28 of the fiber scope 2E and the case of using the field sequential type electronic scope 2A, a field sequential light sequentially switched with three primary colors or a supplementary color system will be required as an illuminating light. The light source apparatus 1 of this embodiment can output both of the above mentioned white color light and field sequential light.

Figure 12:
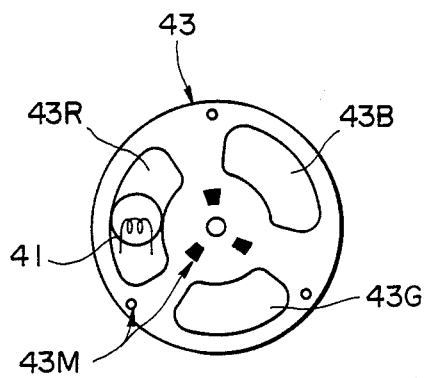

That is to say, as shown in FIG. 1, the light source apparatus 1 comprises such lamp 41 as a xenon lamp or halogen lamp emitting a white color light and lenses 42a and 42b by which the light of this lamp 41 is condensed and is made to enter the entrance end of the light guide 24 of the light source connectors 14E, 14A and 14B to be connected to the light source connector receptacle 15. The above mentioned lamp 41 is controlled by a lighting apparatus 41 in the lighting and lamp current. Between the above mentioned lenses 42a and 42b, as shown in FIG. 12, a color converting filter (called also a rotary filter) 43 having color transmitting filters 43R, 43G and 43B transmitting the three primary colors of R, G and B (or three colors of a supplementary color system) and rotated and driven by a motor 44 is arranged as removably inserted in the light path of the above mentioned lamp 41. By the way, the spaces between the respective color transmitting filters 43R, 43G and 43B of the above mentioned color converting filter 43 are made light intercepting parts. The above mentioned rotary filter 43 and motor 44 are moved by a filter moving means 45.

In order to determine the positions of the respective openings of R, G and B of the above mentioned color converting filter 43, as shown in FIG. 12, the above mentioned color converting filter 43 is provided with opening position detecting marks 43M and an encoder 46 consisting of photoreflectors and photointerrupters detecting the above mentioned opening position detecting marks 43M is provided near this filter 43. A timing signal generating means 47 generating a timing signal of the respective opening periods and light intercepting periods of R, G and B from the detecting output of this encoder 46 is provided. The output signal of the above mentioned timing signal generating means 47 is applied to one input end 48a of a switching switch 48 of two inputs and one output. The other input end 48b of this switching switch 48 is connected to a signal connector receptacle 50 of the light source apparatus 1. The output end 48c of the above mentioned switching switch 48 is connected to the above mentioned lighting apparatus 40. The timing signal from the timing signal generating means 47 through the above mentioned switch 48 and the signal input into the light source apparatus 1 through the signal connector receptacle 50 can be selectively input into the lighting apparatus 40.

The above mentioned light source apparatus 1 is provided with a scope kind selecting means 49 for switching the output light in response to the kind of the scope. This scope kind selecting means 49 consists, for example, of a selecting switch and controls the switching of the above mentioned motor 44, filter moving means 45 and switching switch 48. That is to say, in case a white color light is selected by the above mentioned scope kind selecting means 49, the color converting filter 43 will be retreated from the illuminating light path by the filter moving means 45, the rotation of the motor 44 will be stopped and the switching switch 48 will be set to be conneted on the input end 48b side. On the other hand, in case a field sequential light is selected by the above mentioned scope kind selecting means 49, the color converting filter 43 will be inserted into the illuminating light path by the filter moving means 45, the motor 44 will be rotated and the switching swithch 48 will be set to be connected on the input end 48a side.

In this embodiment, in case a white color light is selected by the above mentioned scope kind selecting means 49, the timing signal from the above mentioned timing signal generating means 47 will not be input into the lighting apparatus 40 and a constant current, for example, of 18 A will be fed to the lamp 41 by this lighting apparatus 40 and therefore the emitted light amount of this lamp 41 will be constant. On the other hand, in case a field sequential light is selected by the above mentioned scope kind selecting means 49, the timing signal from the above mentioned timing signal generating means 47 will be input into the lighting apparatus 40 by which, in response to the above mentioned timing signal, the current fed to the lamp 41 will be increased, for example, to 25 A during the opening period of the color converting filter 43 but will be decreased, for example, to 10 A during the light intercepting period. Therefore, the emitted light amount of the above mentioned lamp 41 will increase during the opening period of the color converting filter 43 but will decrease during the light intercepting period.

Figure 11:
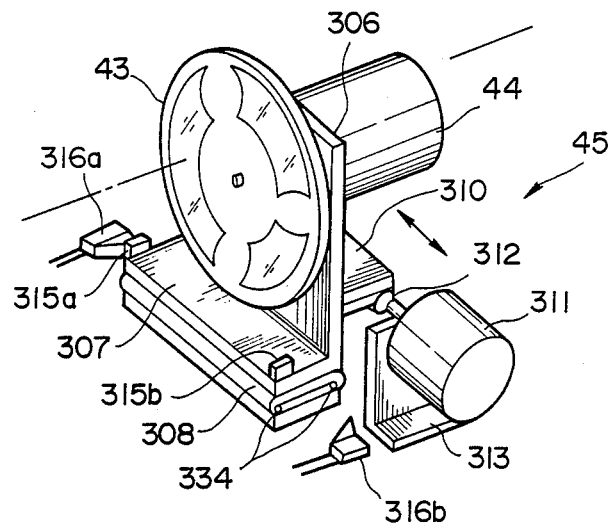

Now, the above mentioned filter moving apparatus 45 is formed as shown, for example, in FIG. 11.

That is to say, the color converting filter 43 and the motor 44 rotating and driving it are fitted to a plate-like fitting bracket 306 below which a flange part 307 bent in the horizontal direction is formed. Two rails 334 fixed on the housing side of the light source apparatus 3 are provided in parallel below this flange part 307. A sliding part 308 in the form of holding these rails 334 from both sides is formed in the bottom of the above mentioned flange part 307 and slidably fits the above mentioned rails 334 so that the above mentioned color converting filter 43 and motor 44 may move.

A rack gear 310 is fitted in the moving direction of the above mentioned color converting filter 43 on the surface on the lamp 41 side of the above mentioned fitting bracket 306 and is meshed with a worm gear 312 rotated by the motor 311. By the way, the motor 311 is fixed on the housing side of the light source apparatus 1 by the bracket 313. By rotating the above mentioned motor 311 normally and reversely, the above mentioned color converting filter 43 can be moved through the above mentioned worm gear 312 and rack gear 310. By the way, the above mentioned motor 311 is controlled by the scope kind selecting means 49.

Flat square pillar-like switch pressing parts 315a and 315b are provided to project on the upper surfaces of both end parts in the moving direction of the flange part 308 of the above mentioned fitting bracket 307. Switching position detecting microswitches 316a and 314b are arranged in the positions pressed by the above mentioned switch pressing parts 315a and 315b at both ends of the above mentioned color converting filter 43 moving range. When these microswitches 316a and 316b are pressed by the above mentioned switch pressing parts 315a and 315b, it will be sensed that the above mentioned color converting filter 43 has reached the end of the moving range, the rotation of the above mentioned motor 311 will be stopped and the color converting filter 43 moving range will be regulated. In the illustrated example, when the switch pressing part 315a presses the microswitch 316a, the white color light from the lamp 41 will pass through the color converting filter 43 and will enter the light guide 24 as a field sequential illuminating light. On the other hand, when the switch pressing part 315b presses the microswitch 316b, the white color light from the lamp 41 will enter the light guide 24 without passing through the above mentioned color converting filter 43.

Figure 7:
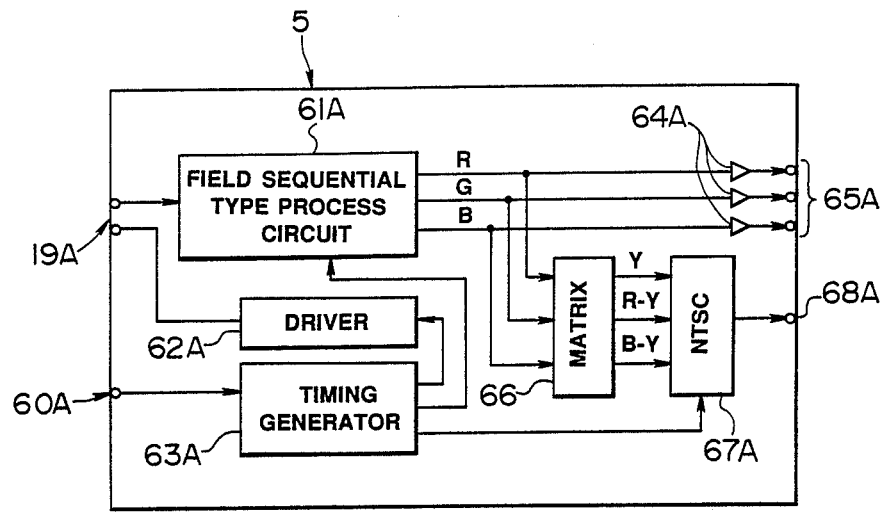

Now, the above mentioned video processor 5 is formed as shown, for example, in FIG. 7.

That is to say, the video processor 5 comprises a field sequential type process circuit 61A processing the output signal of the CCD 31A of the field sequential type electronic scope 2A or externally fitted field sequential type television camera 4A to be a video signal and a driver 62A applying a driving pulse to the above mentioned CCD 31A which are connected respectively to the electric connectors 19A. The output signal of the CCD 31A driven and read out by the above mentioned driver 62A is amplified by the pre-amplifier 33 and is then input into the above mentioned field sequential type process circuit 61A and signals imaged respectively under the field sequential lights, for example, of R, G and B are output as color signals R, G and B which are output respectively as three primary color signals R, G and B from three primary color output ends 65A through drivers 64A. Also, the above mentioned color signals R, G and B are passed through a matrix circuit 66 to produce a luminance signal Y and color difference signals R—Y and B—Y which are then input into an NTSC encoder 67A and are converted to an NTSC system composite video signal which is output from an NTSC output end 68A. By the way, the above mentioned field sequential type process circuit 61A, driver 62A and NTSC encoder 67A are controlled in the timing by a timing generator 63A into which a timing signal from the timing signal generating means 47 of the light source apparatus 1 is input through the above mentioned electric connector receptacle 60A to make a control synchronized with the rotation of the color converting filter 43. The above mentioned field sequential type process circuit 61A is formed as shown, for example, in FIG. 9.

That is to say, the output signal of the CCD 31A input through the pre-amplifier 33 is sample-held in a sample-holding circuit 71, is γ-corrected in a γ correcting circuit 72 and is converted to a digital signal in an A/D converter 73. The signals imaged under the field sequential lights of R, G and B through a multiplexer 74 switched by the signal of the above mentioned timing generator 63A are written respectively into an R frame memory 75R, G frame memory 75G and B frame memory 75B whose signals are simultaneously read out and are converted respectively by D/A converters 76 to analogue color signals R, G and B which are output.

Figure 8:
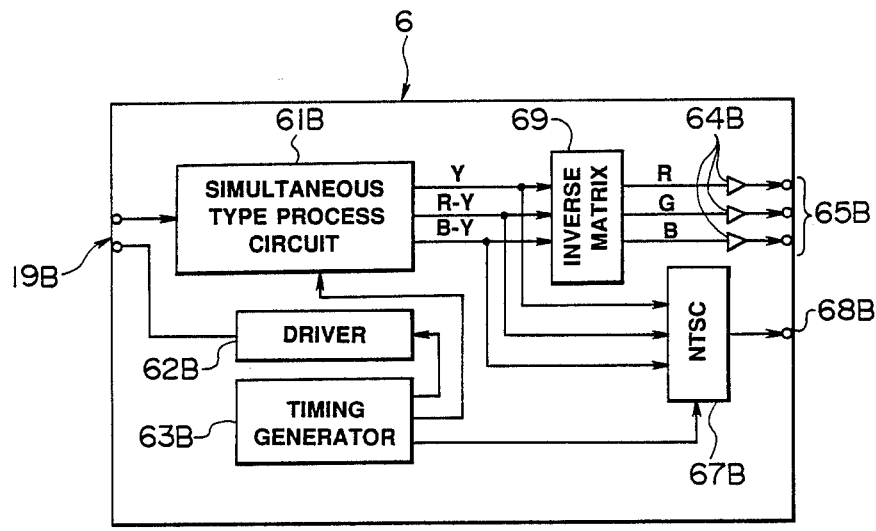
Figure 9:
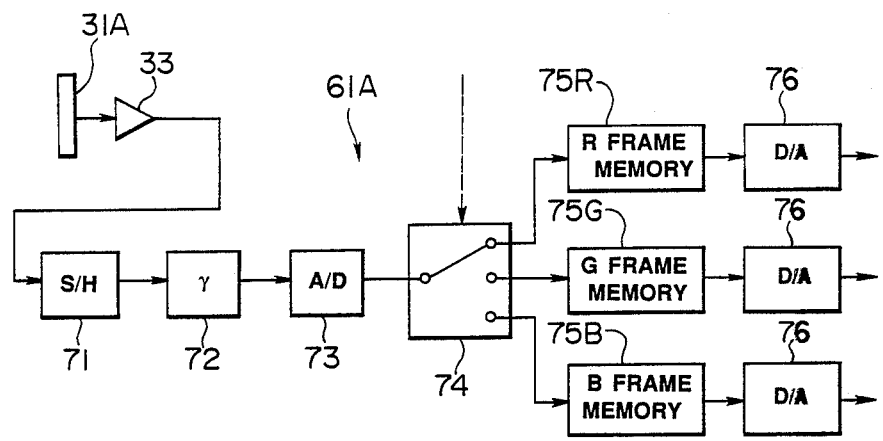

On the other hand, the camera control unit 6 is formed as shown, for example, in FIG. 8.

That is to say, the camera control unit 6 comprises a simultaneous type process circuit 61B processing the output signal of the CCD 31B of the simultaneous type electronic scope 2B or externally fitted simultaneous type television camera 4B to be a video signal and a driver 62 applying a driving pulse to the above mentioned CCD 31B which are connected respectively to electric connector receptacles 19B. The output signal of the CCD 31B driven and read out by the above mentioned driver 62B is amplified by the pre-amplifier 33 and is then input into the above mentioned simultaneous type process circuit 61B to produce, for example, a luminance signal Y and color difference signals R—Y and B—Y which are input into an NTSC encoder 67B and are converted to an NTSC system composite video signal which is output from an NTSC output end 68B. Also, the above mentioned luminance signal Y and color difference signals R—Y and B—Y are input into an inverse matrix circuit 69 and are converted to color signals R, G and B which are output from three primary color output ends 65B through drivers 64B. By the way, the above mentioned simultaneous type process circuit 61B, driver 62B and NTSC encoder 67B are controlled in the timing by a timing generator 63B.

Figure 10:
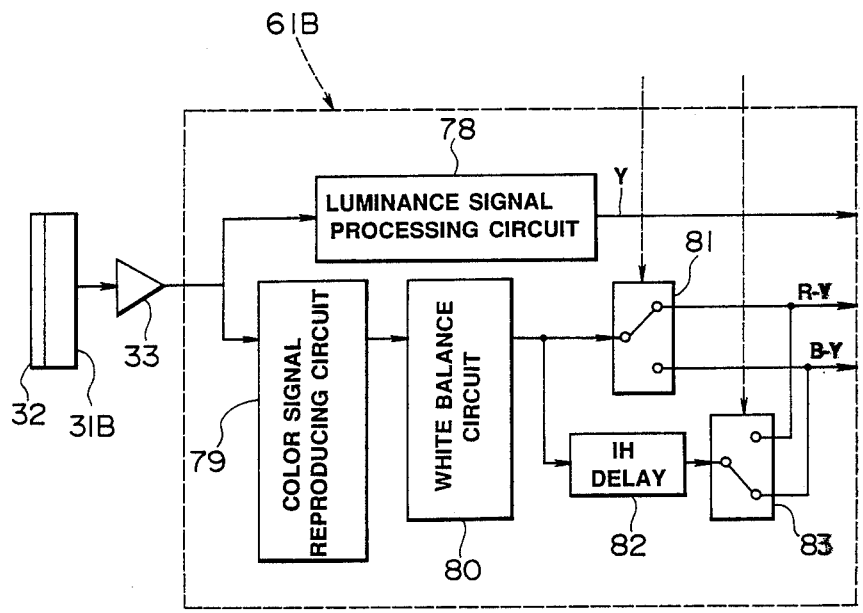

The above mentioned simultaneous type process circuit 61B is formed as shown, for example, in FIG. 10.

That is to say, the output signal of the CCD 31B amplified by the pre-amplifier 33 is input into a luminance signal processing circuit 78 in which a luminance signal Y is produced. The output signal of the above mentioned CCD 31B is input into a color signal reproducing circuit 79 in which color difference signals R—Y and B—Y are produced in time series on each horizontal line. These color difference signals R—Y and B—Y are compensated in the white balance in a white balance circuit 80. One of them is input directly into an analogue switch 81 and the other is delayed by one horizontal line in a 1H delay line 82 and is input into an analogue switch 83. The color difference signals R—Y and B—Y are obtained from the above mentioned analogue switch 81 switched by the switching signal of the timing generator 63.

The operation of this embodiment formed as in the above shall be explained in the following with reference to FIGS. 13 to 17.

In the case of a naked eye observation with the fiber scope 2E, the case of using the externally fitted simultaneous type television camera 4B as connected to the eyepiece part 28 of the fiber scope 2E and the case of using the simultaneous type electronic scope 2B, the light source connector 14E or 14B of the scope 2E or 2B is connected to the light source connector receptacle 15 of the light source apparatus 1. The white color light is selected by the scope kind selecting means 49 of the above mentioned light source apparatus 1. Then, the color converting filter 43 will be retreated from the illuminating light path by the filter moving means 45, the rotation of the motor 44 will be stopped and the switching switch 48 will be connected on the input end 48 side. As shown in FIG. 15(a), at the time of lighting, the lighting apparatus 40 will feed a constant current, for example, of 18 A to the lamp 41 from which a light of a constant light amount will be emitted. This light is condensed as a white color light as it is by the lenses 42a and 42b without passing through the color converting filter 43 and enters the light guide 24 of the above mentioned scope 2E or 2B at the entrance end. This illuminating light is led to the tip part 21 by the light guide 24 and is radiated to an object through the light distributing lens 23. As shown in FIG. 15(b), the illuminating light emitted from this scope tip will be on a constant light amount level. By the way, this light amount level shall be made 1.

On the other hand, in the case of using the externally fitted field sequential type television camera 4A as connected to the eyepiece part 28 of the fiber scope 2E and the case of using the field sequential type electronic scope 2A, the light source connector 14E or 14A of the scope 2E or 2A is connected to the light source connector receptacle 15 of the light source apparatus 1. The field sequential light is selected by the scope kind selecting means 49 of the above mentioned light source apparatus 1. Then, the color converting filter 43 will be inserted into the illuminating light path by the filter moving means 45, the motor 44 will be rotated and the switching switch 48 will be connected on the input end 48a side. As shown in FIG. 16(a), the lighting apparatus 40 will increase the current fed to the lamp 41, for example, to 25 A during the opening period of the color converting filter 43 but will decrease the current, for example, to 10 A during the light intercepting period. Therefore, the emitted light amount of the above mentioned lamp 41 will increase during the opening period of the color converting filter 43 but will decrease during the light intercepting period. This light passes through the color converting filter 43 to be converted to field sequential lights of R, G and B which are condensed by lenses 42a and 42b and enter the light guide 24 of the above mentioned scope 2E or 2A at the entrance end. This illuminating light is led to the tip part 21 by the light guide 24 and is radiated to an object through the light distributing lens 23. As shown in FIG. 16(b), the illuminating light emitted from this scope tip will be an intermittent light of a light amount level of 1.5 about 1.5 times as large as the light amount at the time of the white color light output.

Figure 17:
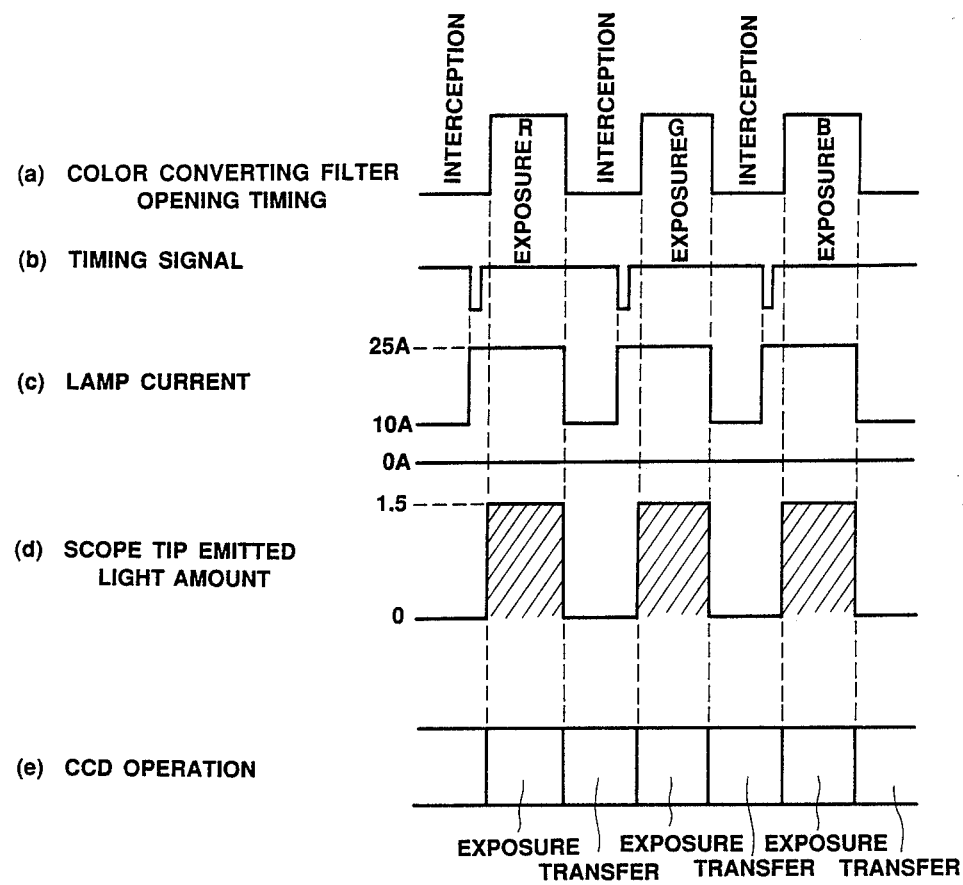

FIG. 17 shows the timing of the operation of the lamp 41, color converting filter 43 and field sequential type CCD 31A at the time of the field sequential light output. As shown in FIG. 17(a), the color converting filter 43 repeats alternately the light interception and exposure and the transmitted wavelength range at the time of the exposure is switched sequentially to R, G and B. As shown in FIG. 17(b), a timing signal showing the timing of the beginning of the respective exposure periods of R, G and B will be output from the timing signal generating means 47 and will be input into the lighting apparatus 40. As shown in FIG. 17(c), in response to the above mentioned timing signal, the current fed to the lamp 41 from the above mentioned lighting apparatus 40 will increase to 25 A during the exposure period of the color converting filter 43 but will decrease to 10 A during the interception period. As shown in FIG. 17(d), in response to the fluctuation of the current, the light amount emitted from the tip of the scope will increase to be on a level of 1.5 during the exposure period of the color converting filter 43 but will be on a level of 0 during the interception period. As shown in FIG. 17(e), the exposure period and interception period of the above mentioned color converting filter 43 are synchronized with the exposure period of the CCD 31 of the field sequential type electronic scope 2A or externally fitted field sequential type television camera 4A and the transfer period of the signal charge. Therefore, the illuminating light amount will be on a level of 1.5 during the exposure period of the CCD 31A but will be on a level of 0 during the interception period of the CCD 31A.

Figures 13, 14, 15, 16:
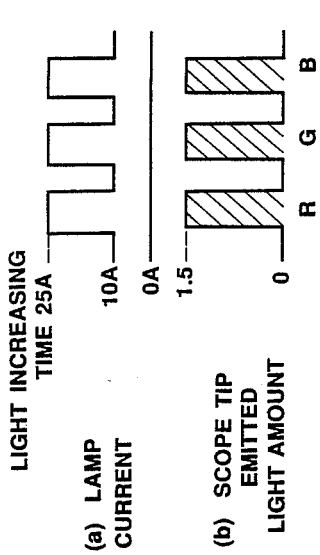

FIGS. 13 and 14 show the case that the light amount of the lamp 41 is made constant at the time of outputting a white color light and at the time of outputting a field sequential light for comparison. As shown in FIG. 13, the white color light outputting time in this case is the same as the white color light outputting time in this embodiment. On the other hand, at the field sequential light outputting time, as shown in FIG. 14(a), the current fed to the lamp 41 is constant at 18 A the same as at the white color light outputting time and therefore, as shown in FIG. 14(b), the illuminating light emitted from the scope tip will be an intermittent light on the same light amount level of 1 as of the light amount at the white color light outputting time. Therefore, the total light amount will reduce to be less than at the white color light outputting time and the light amount at the time of observation will be short.

On the other hand, in this embodiment, as shown in FIGS. 16 and 17, the field sequential light will be an intermittent light on a light amount level of 1.5 and therefore the light amount will not be short. Further, during the light interception period of the color converting filter 43, that is, during the charge transfer period of the CCD 31A, the lamp current will be reduced to 10A, therefore the total power consumption of the lamp 41 will not be substantially varied as compared with that at the white color light outputting time and the light amount will be to be increased.

During the light interception period of the color converting filter 43, the light amount of the lamp 41 will be reduced and therefore, even at the field sequential light outputting time, the light emitted from the lamp 41 will be able to be effectively utilized.

Also, the life of the lamp 41 can be elongated.

By the way, the operation at the field sequential light outputting time of the light source apparatus of this embodiment can be applied not only to the field sequential type electronic scope 2A or externally fitted field sequential type television camera 4A having the field sequential type CCD 31A but also to the simultaneous type electronic scope or externally fitted simultaneous type television camera using a line transfer system CCD having charge transfer periods as shown, for example, in FIG. 17(e). That is to say, in this case, during the exposure period of the CCD, the light amount of the lamp 41 may be increased and, during the charge transfer, the light amount of the lamp 41 may be decreased. Thereby, the same as at the time of using the field sequential type electronic scope or externally fitted field sequential type television camera, without substantially varying the total power consumption, the light amount can be increased.

Also, a white color light and field sequential light can be treated with one lamp 41, the formation is simple and the light source apparatus can be made small.

Figure 18:
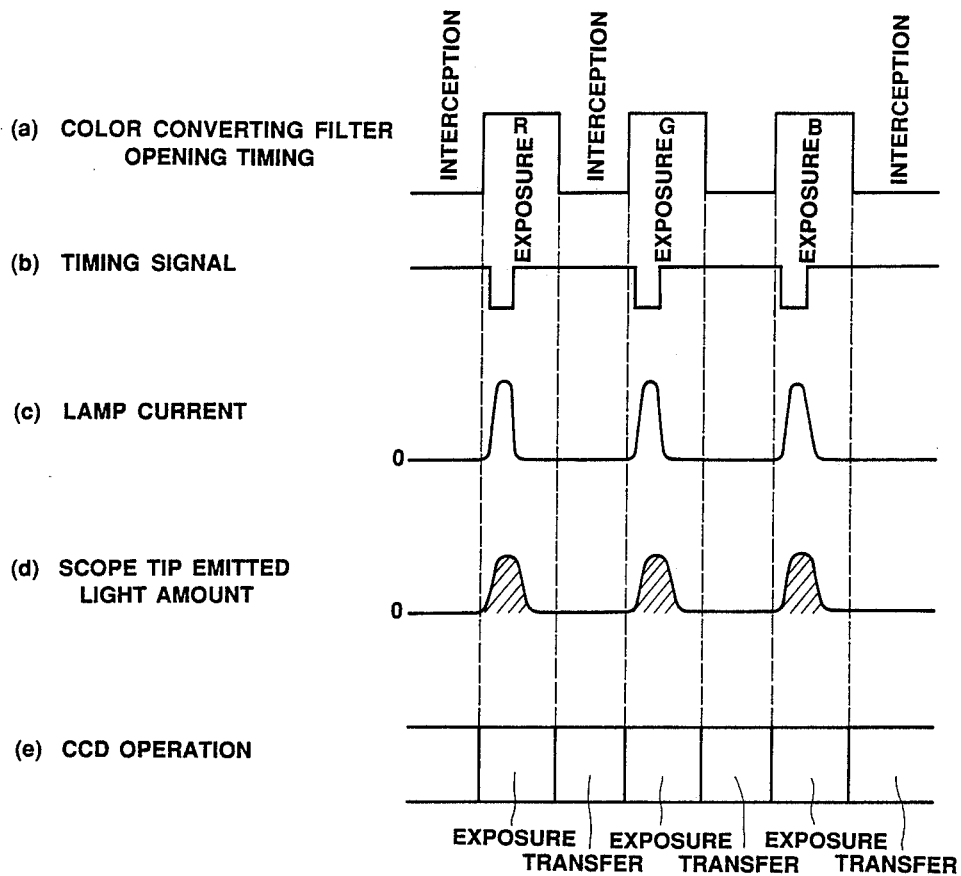
FIG. 18 is a timing chart showing the operation of an endoscope light source apparatus of the second embodiment of the present invention.

FIG. 18 is a timing chart showing the operation of an endoscope light source apparatus of the second embodiment of the present invention.

In this embodiment, such lamp which can emit a strobolight as a strobolamp or LED is used for the lamp 41.

As shown in FIGS. 18(a) and (e), the timing of the operation of the color converting filter 43 and CCD 31A is the same as in the first embodiment. In this embodiment, as shown in FIG. 18(b), during the exposure period of the color converting filter 43, a timing signal will be generated from a timing signal generating means 47. In response to this timing signal, a lamp current will be intermittently fed to the above mentioned lamp 41 from the lighting apparatus 40. As shown in FIG. 18(d), in response to the above mentioned lamp current, during the exposure period of the color converting filter 43, that is, during the exposure period of the CCD 31A, a light will be intermittently emitted from this lamp 41 and will be projected from the tip of the scope.

In the first embodiment, a xenon lamp or halogen lamp is used for the lamp 41. Therefore, once the lamp is extinguished, it will take time until the lamp is lighted again. Therefore, without extinguishing the lamp, the lamp current is varied, for example, to 10 A and 25 A.

On the other hand, according to this embodiment, as an extinguishable strobolamp or LED is used for the lamp 41, during the charge transfer of the CCD 31A, the lamp current will be made 0 and the lamp 41 will be extinguished. Therefore, the light emitting energy of the lamp 41 can be effectively utilized and the light source apparatus can be made small and light.

The other formations, operations and effects are the same as in the first embodiment.

Figure 19:
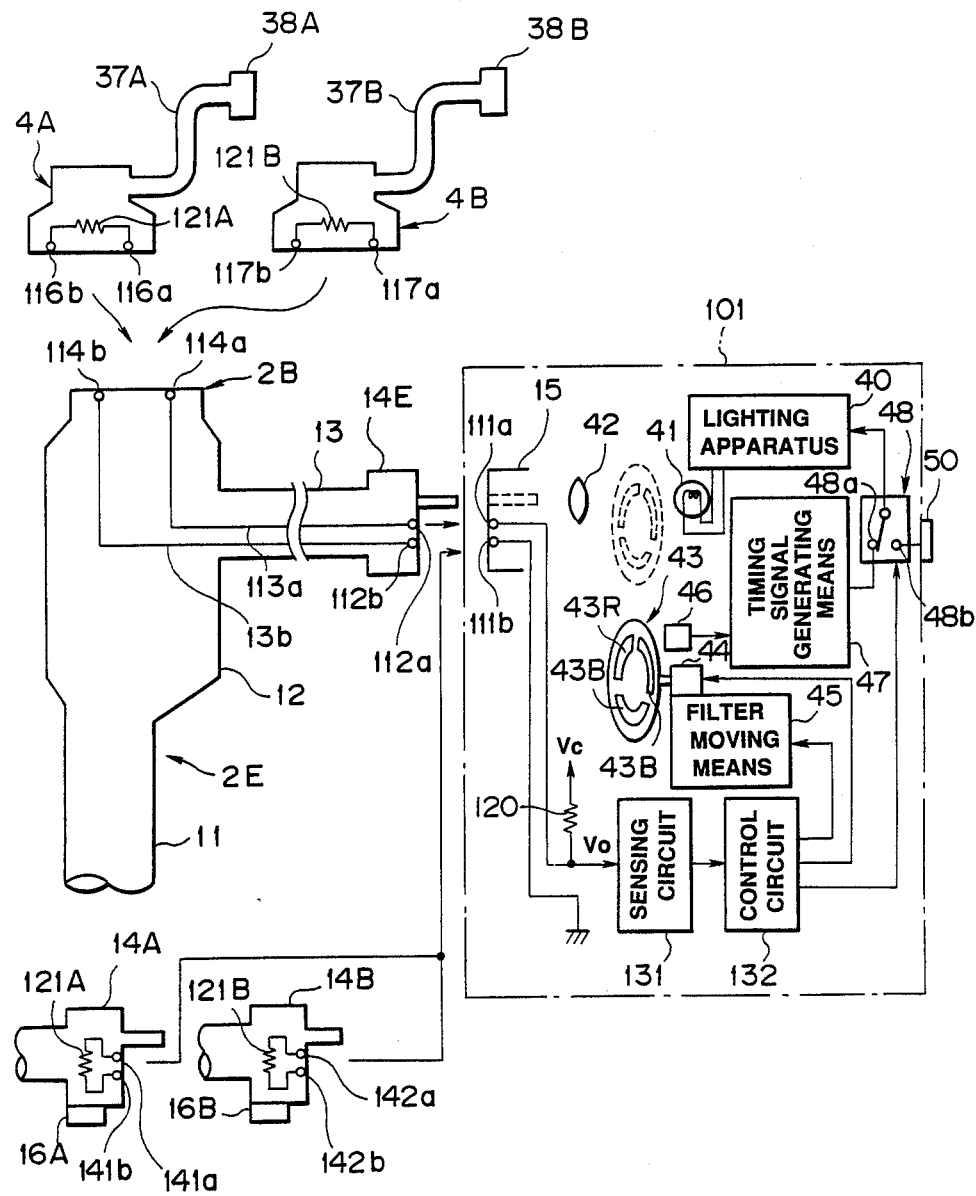
FIG. 19 is an explanatory view showing an endoscope system in the third embodiment of the present invention.

FIG. 19 is an explanatory view showing an endoscope system in the third embodiment of the present invention.

In this embodiment, the kind of a scope or externally fitted television camera can be sensed automatically.

A light source connector receptacle 15 of an endoscope light source apparatus 101 of this embodiment is provided with terminals 111a and 111b. A current source voltage Vc is applied through a resistance 120 to one terminal 111a which is connected to a sensing circuit 131. The sensing output of the above mentioned sensing circuit 131 is input into a control circuit 132 which controls a motor 44, filter moving means 45 and switch 48.

On the other hand, a light source connector 14E of a fiber scope 2E is provided with terminals 112a and 112b to be connected respectively to the terminals 111a and 111b of the above mentioned light source connector receptacle 15. An eyepiece part 28 is provided with a terminal 114a connected to the above mentioned terminal 112a through a signal line 113a and a terminal 114b connected to the above mentioned terminal 112b through a signal line 113b.

Also, an externally fitted field sequential television camera 4A is provided with terminals 116a and 116b to be connected respectively to the terminals 114a and 114b provided in the above mentioned eyepiece part 28. These terminals 116a and 116b are connected with each other through a resistance 121A. An externally fitted simultaneous type television camera 4B is provided with terminals 117a and 117b to be connected respectively to the terminals 114a and 114b provided in the above mentioned eyepiece part 28. These terminals 117a and 117b are connected with each other through a resistance 121B.

If the resistance values of the above mentioned resistances 120, 121A and 121B are respectively R120, R121A and R121B, these resistance values will be set, for example, to be:

$$R120 = R121A << R121B$$

The above mentioned sensing circuit 131 has a voltage $V_o$ in the above mentioned terminal 111a applied to a non-inverted input end of a comparator not illustrated and has a reference voltage $V_{REF}$ applied to an inverted input end. This reference voltage $V_{REF}$ is set to be between $V_c$ and $\frac{1}{2} V_c$, for example, at $\frac{2}{3} V_c$. The comparative output $V_o$ of the above mentioned comparator is input into the control circuit 132.

In case the output $V_o$ of the above mentioned comparator is of an H signal, by the above mentioned control circuit 132, as indicated by the solid lines in FIG. 19, the color converting filter 43 will be retreated from the illuminating light path, the rotation of the motor 44 will be stopped and the switching switch 48 will be connected on the input end 48b side. On the other hand, in case the above mentioned output $V_o$ is of an L signal, by the above mentioned control circuit 132, as indicated by the broken lines in FIG. 19, the color converting filter 43 will be inserted into the illuminating light path, the motor 44 will be rotated, the means 45 will be controlled and the switching switch 48 will be connected on the input end 48a side.

The light source connector 14A of the field sequential type electronic scope 2A is provided with terminals 141a and 141b to be connected respectively to the terminals 111a and 111b of the above mentioned light source connector receptacle 15. These terminals 141a and 141b are connected with each other through a resistance 121A of a resistance value R121A. In the same manner, the light source connector 14B of the simultaneous type electronic scope 2B is provided with terminals 142a and 142b to be connected respectively to the terminals 111a and 111b of the above mentioned light source connector receptacle 15. These terminals 142a and 142b are connected with each other through a resistance 121B of a resistance value R121B.

By the way, in this embodiment, one condenser lens 42 is provided instead of two lenses 42a and 42b.

The other formations are the same as in the first embodiment.

In this embodiment, when the externally fitted field sequential type television camera 4A is connected to the eyepiece part 28 of the fiber scope 2E and the light source connector 14 of the above mentioned fiber scope 2E is connected to the light source connector receptacle 15 of the light source apparatus 101, the terminals 111a and 111b of the light source connector receptacle 15 and the terminals 112a and 112b of the light source connector 14 will be connected respectively with each other and the terminals 114a and 114b of the eyepiece part 28 and the terminals 116a and 116b of the externally fitted field sequential type television camera 4A will be connected respectively with each other. Therefore, $$V_o = V_c \cdot R\,121A/(R\,120 + R\,121A)$$
$$= \tfrac{1}{2} V_c \ (R\,120 = R\,121A)$$

will be applied to the sensing circuit 131 of the above mentioned light source apparatus 101. This voltage $V_o$ will be compared with the reference voltage $V_{REF}$ by the comparator and, from $V_o = \tfrac{1}{2}V_c < \tfrac{2}{3}V_c$, the output $V_o$ of the comparator will be an L signal. Therefore, the color converting filter 43 will be inserted into the illuminating light path and a field sequential light will be output from the light source apparatus 101. In this case, the same as in the first embodiment, the lamp 41 will increase the light during the exposure period of the color converting filter 43 but will decrease the light during the interception period.

On the other hand, when the externally fitted simultaneous type television camera 4B is connected to the eyepiece part 28 of the above mentioned fiber scope 2E and the light source connector 14E of the above mentioned fiber scope 2E is connected to the light source connector receptacle 15 of the light source apparatus 101, the terminals 111a and 111b of the light source connector receptacle 15 and the terminals 112a and 112b of the light source connector 114E will be connected respectively with each other and the terminals 114a and 114b of the eyepiece part 28 and the terminals 117a and 117b of the externally fitted simultaneous type television camera 4B will be connected respectively with each other. Therefore, $$V_o = V_c \cdot R\ 121B/(R\ 120 + R\ 121B)$$
$$\approx V_c\ (R\ 120 << R\ 121B)$$

will be applied to the sensing circuit 131 of the above mentioned light source apparatus 3. This voltage $V_o$ will be compared with the reference voltage $V_{REF}$ by the comparator and, from $V_o \approx V_c > \frac{2}{3}V_c$, the output $V_o$ of this comparator will be an H signal. Therefore, the color converting filter 43 will be retreated from the illuminating light path and a white color light will be output from the light source apparatus 101. In this case, the light amount of the lamp 41 will be constant the same as in the first embodiment.

When the television cameras 4A and 4B are not connected to the eyepiece part 28 of the above mentioned fiber scope 2F but the light source connector 14 of the above mentioned fiber scope 2F is connected to the light source connector receptacle 15 of the light source apparatus 101, the terminals 111a and 111b of the light source receptacle 15 will be opened and $V_o = V_c$ will be applied to the sensing circuit 131 of the light source apparatus 101. This voltage $V_o$ will be compared with the reference voltage $V_{REF}$ by the comparator and, from $$V_o = V_c > \tfrac{2}{3}V_c$$

the output $V_o$ of this comparator will be an H signal. Therefore, the color converting filter 43 will be retreated from the illuminating light path and a white color light will be output from the light source apparatus 101.

In case the light source connector 14A of the field sequential type electronic scope 2A is connected to the light source connector receptacle 15 of the above mentioned light source apparatus 101, the operation will be the same as in the case of the externally fitted field sequential type television camera 4A. In case the light source connector 14B of the simultaneous type electronic scope 2B is connected to the light source connector receptacle 15 of the above mentioned light source apparatus 101, the operation will be the same as in the case of the externally fitted simultaneous type television camera 4B.

Thus, according to this embodiment, by detecting the kind of the scope connected to the light source apparatus 101 and the kind of the externally fitted television camera in the case of the fiber scope 2E, the illuminating light adapted to the connected scope or externally fitted television camera can be automatically fed.

The other operations and effects are the same as in the first embodiment.

Figure 20:
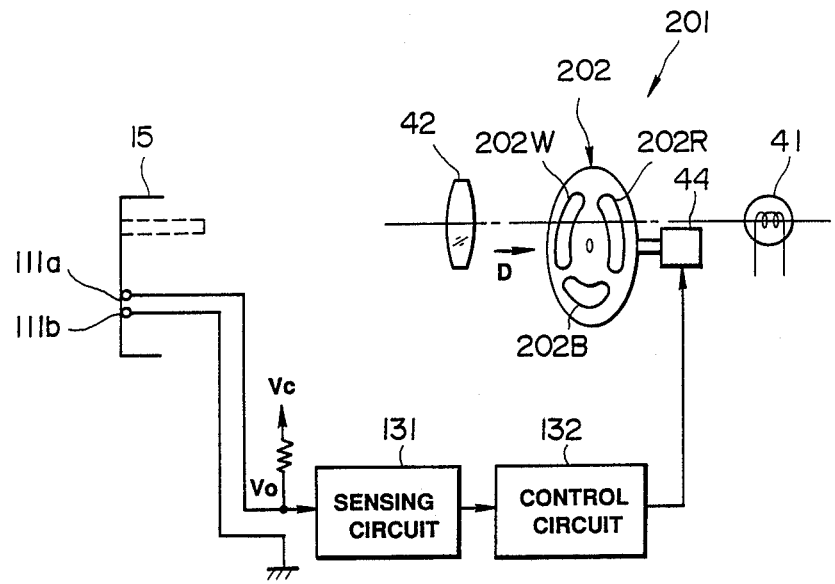
FIGS. 20 to 22 relate to the fourth embodiment of the present invention.
Figure 21:
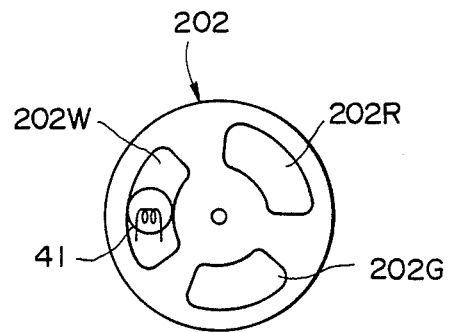
Figure 22:
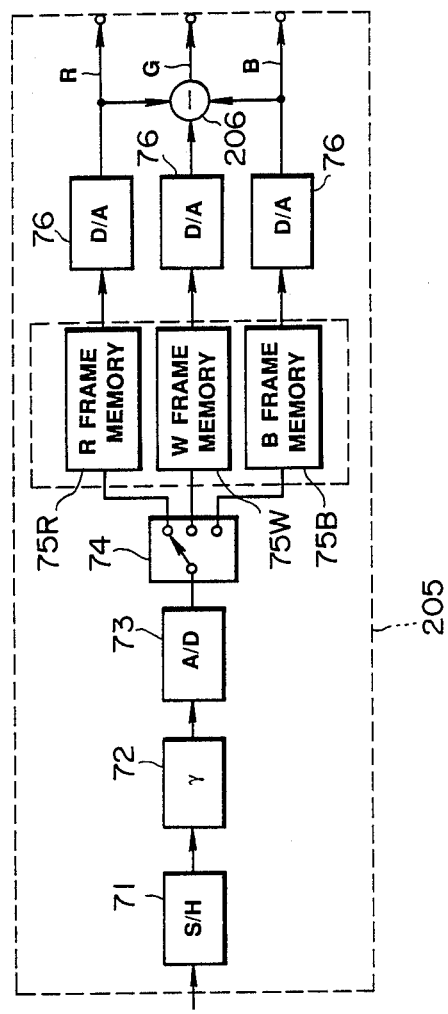

The fourth embodiment of the present invention is shown in FIGS. 20 to 22.

In an endoscope light source apparatus 201 in this embodiment, a color converting filter 202 rotated and driven by a motor 44 is arranged in the light path between the lamp 41 and condenser lens 42 and has a filter 202W transmitting a white color light and two kinds of filters transmitting primary color lights or supplementary color lights, for example, filters 202R and 202B transmitting color lights of R and B.

In response to the sensing output of a sensing circuit 131, a control circuit 132 controls the rotation/stop of the motor 44 rotating and driving the above mentioned color converting filter 202. That is to say, by the above mentioned control circuit 132, in case the field sequential type electronic scope 2A or the fiber scope 2E fitted with the externally fitted field sequential type television camera 4A is connected to the light source apparatus 201 and the output of the sensing circuit 131 is an L signal, so that a field sequential light may be output, the color converting filter 202 will be rotated at a predetermined frequency and, in case the simultaneous type electronic scope 2B, the fiber scope 2E fitted with the externally fitted simultaneous type television camera 4B or the fiber scope 2E not fitted with the television cameras 4A and 4B is connected to the light source apparatus 201 and the output of the sensing circuit 131 is an H signal, as shown in FIG. 21, the color converting filter 202 will be stopped in the position in which the filter 202W is interposed in the light path of the lamp 41. Therefore, in case the externally fitted field sequential type television camera 4A is connected to the eyepiece part 28 of the fiber scope 2E, field sequential lights of R, W and B will be emitted. On the other hand, in case the television cameras 4A and 4B are not connected or the externally fitted simultaneous type television camera 4B is connected to the eyepiece part 28 of the fiber scope 2E, the white color light from the lamp 41 will pass through the filter 202W and, as a result, a white color light will be emitted.

By the way, in order to stop in a predetermined position, the above mentioned color converting filter 202 is provided with a rotating position sensor not illustrated. This rotating position sensor is formed, for example, of an arcuate slot provided on the outer peripheral side of the filter 202W and a photosensor arranged to be opposed to this slot so that the position of the filter 202W may be sensed by sensing the above mentioned slot with the photosensor.

Also, in this embodiment, as the field sequential illuminating lights are not of R, G and B, the field sequential type process circuit 205 in the video processor 5 is formed as shown, for example, in FIG. 22.

That is to say, a W frame memory 75W is provided instead of the G frame memory 75G of the field sequential type process circuit 61A in the first embodiment. The same hard frame memory as the G frame memory though different in the memory contents can be used for the above mentioned W frame memory 75W. The W color signal read out of the above mentioned W frame memory 75W and converted to an analogue signal by the D/A converter 76 is input into a subtracter 206, has the R color signal and B color signal subtracted and produces a G color signal. The others are the same as in the field sequential type process circuit 61A shown in FIG. 9.

Thus, in this embodiment, the rotary filter 202 is provided with a filter 202W transmitting a white color light, field sequential lights including the white color light can be output and, by stopping the color converting filter 202 in the position in which the above mentioned filter 202W is interposed in the light path of the lamp 41, a white color light can be also output.

According to this embodiment, no means of moving the color converting filter is required to be provided, the cost can be reduced and the size can be made small.

The other formations, operations and effects are the same as in the third embodiment.

By the way, in this embodiment, the field sequential illumination is made in R, W and B but is not limited to this. The illumination may be made, for example, in R, G, W; W, G, B; Cy (cyan), Ye (yellow), W; Cy, W, Mg (magenta); W, Ye, Mg.

Figure 23:
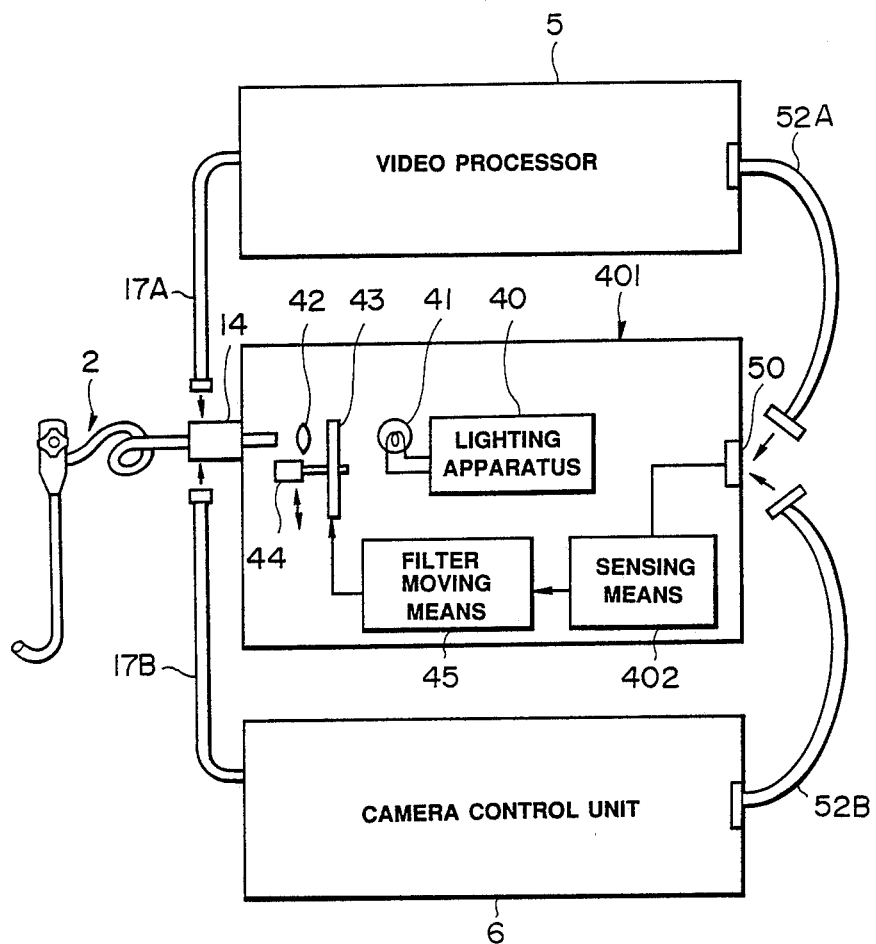
FIG. 23 is an explanatory view showing an endoscope system in the fifth embodiment of the present invention.

The fifth embodiment of the present invention is shown in FIG. 23.

In this embodiment, a field sequential light and white color light are switched by sensing that the video processor 5 or camera control unit 6 has been connected to the light source apparatus.

An endoscope light source apparatus 401 of this embodiment is provided with a sensing means 402 sensing whether the video processor 5 has been connected to the electric connector receptacle 50 through the rear cable 52A or whether the camera control unit 6 has been connected through the rear cable 52B. By the way, the above mentioned rear cables 52A and 52B are to transmit and receive the signal of a freezing and releasing foot switch not illustrated or the like and the signal for rotating and controlling the color converting filter 43 or the like between the light source apparatus 401 and video processor 5 and between the light source apparatus 401 and camera control unit 6. The formation of the above mentioned connection sensing means 402 is the same as of the connection sensing means shown, for example, in FIGS. 19 and 20. The above mentioned connection sensing means 402 may detect whether a signal is transmitted through the rear cables 52A and 52B and may sense which of the video processor 5 and camera control unit 6 is connected.

The above mentioned sensing means 402 controls the filter moving means 45 on the basis of the sensing result. That is to say, in case the sensing means 402 senses that the video processor 5 has been connected to the light source apparatus 401, it will control the filter moving means 45 to insert the color converting filter 43 into the illuminating light path and, in case it senses that the camera control unit 6 has been connected to the light source apparatus 401 and in case it senses that neither of the video processor 5 and camera control unit 6 is connected to the light source apparatus 401, the sensing means 402 will control the filter moving means 45 to retreat the color converting filter 43 from the illuminating light path.

Though not illustrated, the same as in the third embodiment, on the basis of the sensed result of the above mentioned sensing means 402, the lighting apparatus 40 will be controlled so that, when the video processor 5 is connected, the lamp 41 will intermittently increase the light amount as synchronized with the operation of the field sequential type imaging means and, when the camera control unit 6 is connected, the lamp 41 will continuously emit a light.

By the way, in FIG. 23, the reference numeral 2 generally represents the respective scopes 2E, 2A and 2B and the reference numeral 14 generally represents the respective light source connectors 14E, 14A and 14B.

Therefore, in case the video processor 5 is connected to the light source apparatus 401, a field sequential light will be output and, in case the camera control unit 6 is connected to the light source apparatus 401 and in case neither of the video processor 5 and camera control unit 6 is connected, a white color light will be output.

Thus, according to this embodiment, an illuminating light adapted to the used scope can be automatically fed.

The other formations, operations and effects are the same as in the first embodiment.

Figure 24:
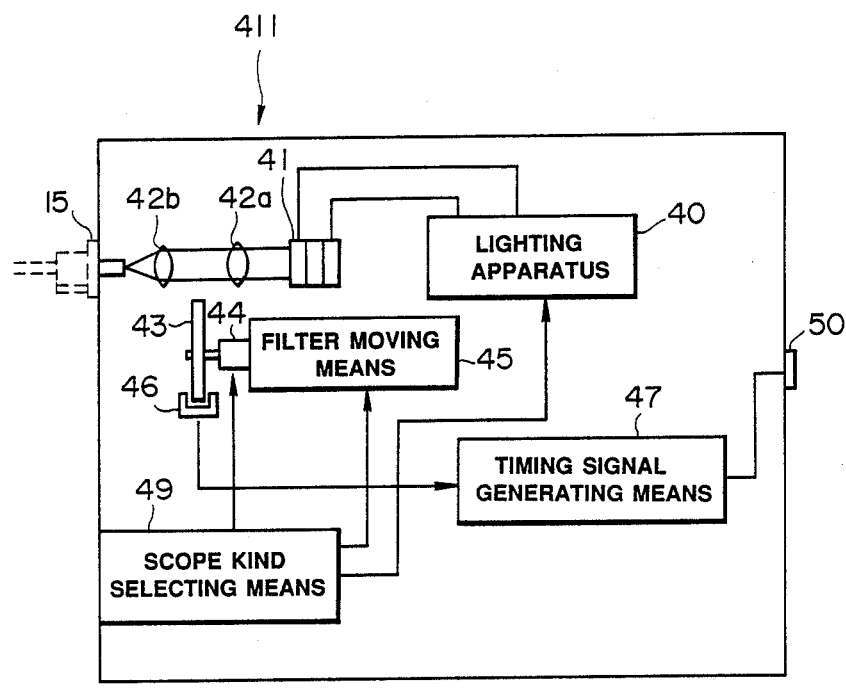
FIGS. 24 to 26 relate to the sixth embodiment of the present invention.
Figure 25:
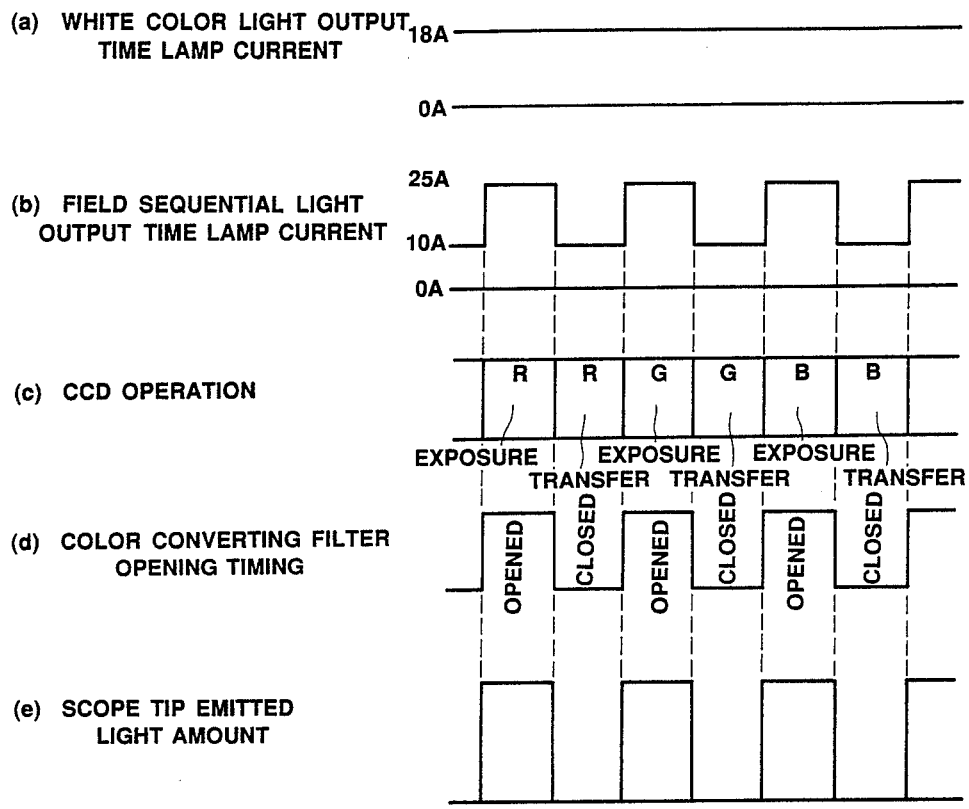
Figure 26:
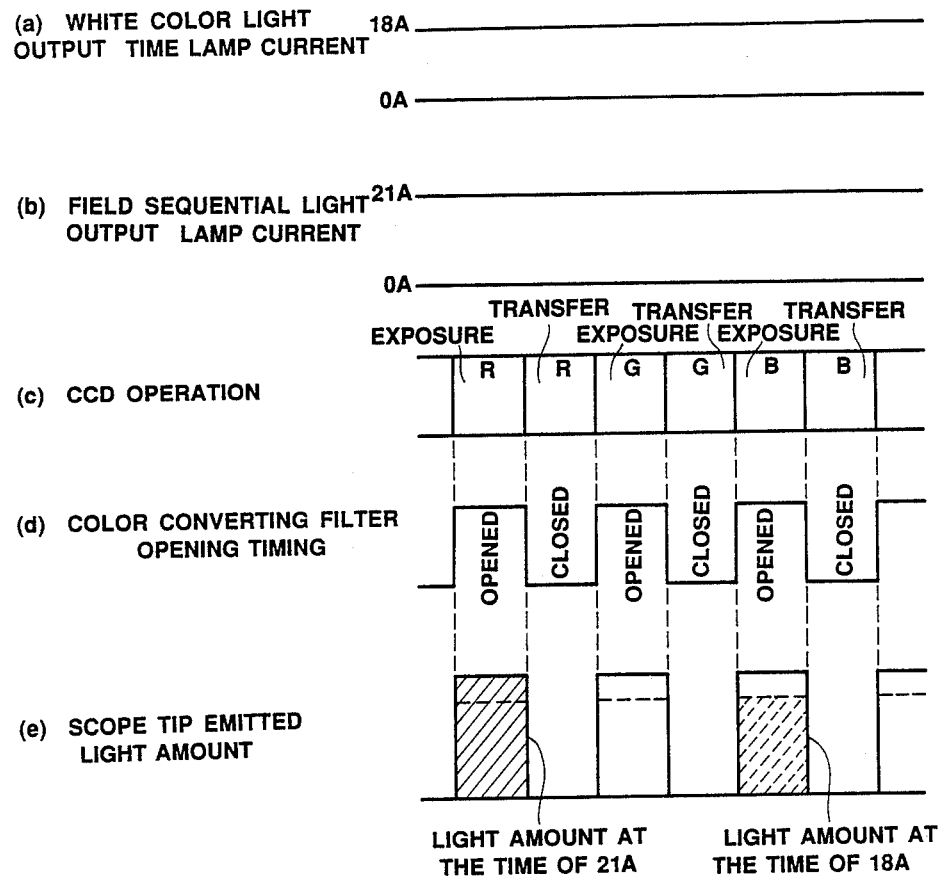

The sixth embodiment of the present invention is shown in FIGS. 24 to 26.

As shown in FIG. 24, in an endoscope light source apparatus 411 of this embodiment, as different from the other embodiments in the above, no timing signal from the timing signal generating means 47 is input into the lighting apparatus 40 and, even when a field sequential light is output, this lighting apparatus 40 will feed no pulse-like current to the lamp 41. Instead, the above mentioned lighting apparatus 40 is controlled by the scope kind selecting means 49 and the size of the current fed to the lamp 41 will be switched at the time of outputting a white color light and at the time of outputting a field sequential light.

The other formations are the same as in the first embodiment.

The operation of this embodiment shall be explained in the following with reference to FIGS. 25 and 26 while comparing it with the operation of another embodiment.

In the other embodiment and this embodiment, when a white color light is output, that is, when the simultaneous type electronic scope 2B is used, when a naked eye observation is made with the fiber scope 2E and when the simultaneous type television camera 4B, a still camera or cine camera is fitted to the eyepiece part 28 of the above mentioned fiber scope 2E, as shown in FIGS. 25(a) and 26(a), a constant current, for example, of 18 A will be fed to the lamp 41.

On the other hand, when a field sequential light is output, that is, when the field sequential type electronic scope 2A is used and when the field sequential type television camera 4A is fitted to the eyepiece part 28 of the fiber scope 2E, in the other embodiment, as shown in FIGS. 25(b) to (d), during the exposure period of the CCD, that is, during the opening period of the color converting filter 43, the current fed to the lamp 41 will be increased, for example, to 25 A and during the light intercepting period, the current will be decreased, for example, to 10 A. Thereby, as shown in FIG. 25(e), the light emitted from the tip of the scope will become an intermittent light larger in the peak light amount than the white color light. By such operation, the lamp life can be elongated without increasing the power consumption.

On the other hand, in this embodiment, when a field sequential light is output, as shown in FIGS. 26(b) to (d), irrespective of the CCD operation and the opening timing of the color converting filter 43, a constant current, for example, of 21 A larger than the lamp current at the time of outputting the white color light will be fed to the lamp 41. Thereby, as shown in FIG. 26(e), the light emitted from the tip of the scope will become an intermittent light larger in the peak light amount than the white color light.

If the current source capacity has a space and there will be no problem in the actual use even if the life of the lamp 41 more or less decreases, as in this embodiment, when a field sequential light is output, a constant current larger than when a white color light is output may be fed to the lamp 41. Thereby, even if the lamp 41 is not pulse-lighted, the emitted light will be able to be made light, that is to say, when a field sequential light is output, the peak light amount will be able to be increased to be larger than when a white color light is output and, even when the field sequential light is output, a sufficient light amount will be able to be fed.

By the way, this embodiment can be applied to the third to fifth embodiments. That is to say, when a field sequential light is output, without intermittently increasing the light of the lamp 41, the light amount may be increased to be larger than when a white color light is output.

Figure 27:
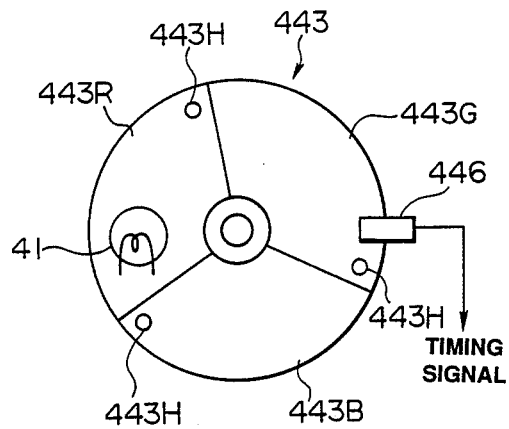
FIGS. 27 to 29 relate to the seventh embodiment of the present invention.
Figure 28:
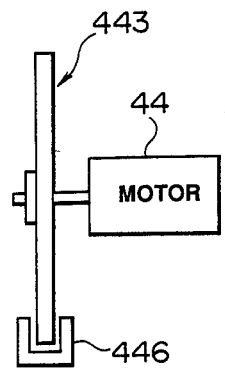
Figure 29:
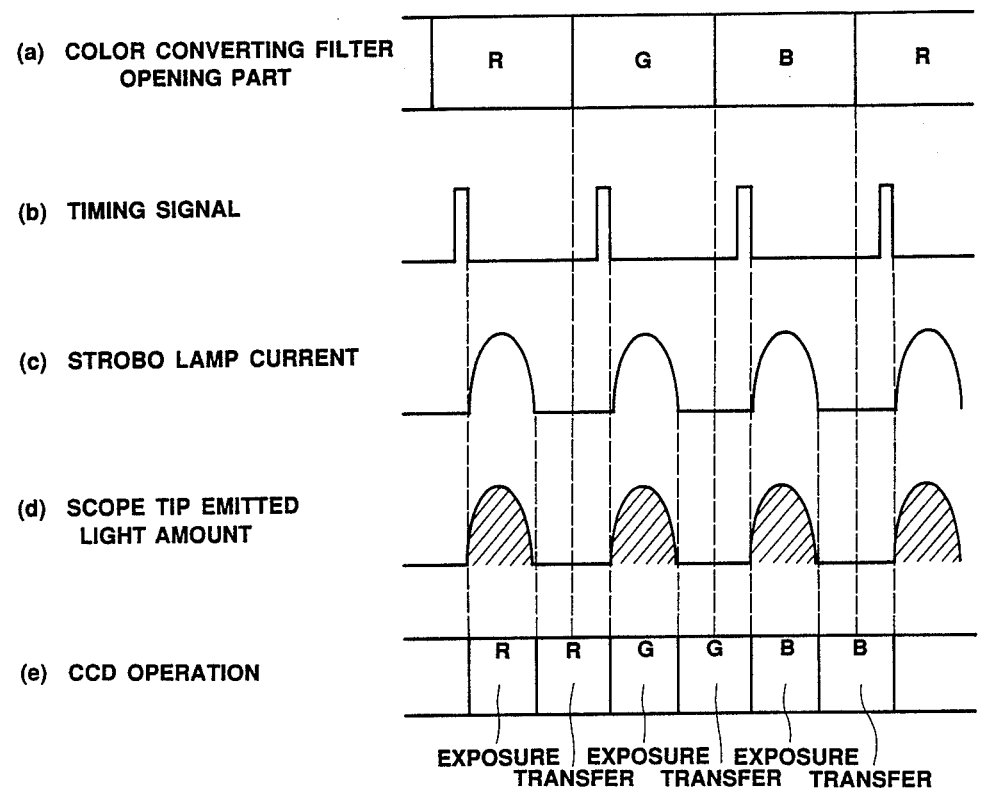

The seventh embodiment of the present invention is shown in FIGS. 27 to 29.

In this embodiment, such color converting filter 443 having no light intercepting part as is shown in FIG. 27 is used instead of such color converting filter 43 having light intercepting parts as is shown in FIG. 12. The other formations are the same as in the first to fifth embodiments in which the light amount will intermittently increase when a field sequential light is output. However, in this embodiment, such strobolamp as in the second embodiment is used for the lamp 41.

In the above mentioned color converting filter 443, filters 443R, 443G and 443B transmitting respective colors of R, G and B are formed by being evaporatively deposited on such disc-like transparent material as of glass. No particular light intercepting part is provided on the boundaries of the above mentioned respective color transmitting filters 443R, 443G and 443B. A timing detecting hole 443H is provided in a part of each of the respective color transmitting filters 443R, 443G and 443B. As shown in FIGS. 27 and 28, a rotary position detecting means 446 consisting of a photoreflector or photointerrupter is provided to be opposed to the above mentioned hole 443H. A timing signal is generated by this rotary position detecting means 446.

The operation of this embodiment at the time of outputting a field sequential light shall be explained in the following with reference to FIG. 29.

As shown in FIG. 29(a), when a field sequential light is output, the respective color transmitting filters of R, G and B of the color converting filter 443 will be sequentially inserted into the illuminating light path but there will be no light intercepting period. With the rotation of the above mentioned color converting filter 443, such timing signal as is shown in FIG. 29(b) will be generated by the rotary position detecting means 446. In response to this timing signal, such intermittent current as is shown in FIG. 29(c) will be fed to the strobolamp 41 which will intermittently emit a light and, as shown in FIG. 29(d), the light emitted from the tip of the scope will become an intermittent light. There is a predetermined extinguished light period after the light emission of the above mentioned strobolamp 41 ends until the next light emission begins. Also, as shown in FIG. 29(e), the field sequential type CCD 31A will be exposed to the light to accumulate the charge during the light emission of the above mentioned strobolamp 41 and will transfer the charge simultaneously with the end of the light emission of the strobolamp 41. Thus, the CCD 31a makes an exposure and transfer in the order of R, G and B as synchronized with the timing of R, G and B of the color converting filter 443.

Thus, by intermittently lighting the lamp 41 when a field sequential light is emitted, no light intercepting part is required on the color converting filter.

The other operations and effects are the same as in the first to fifth embodiments.

Figure 30:
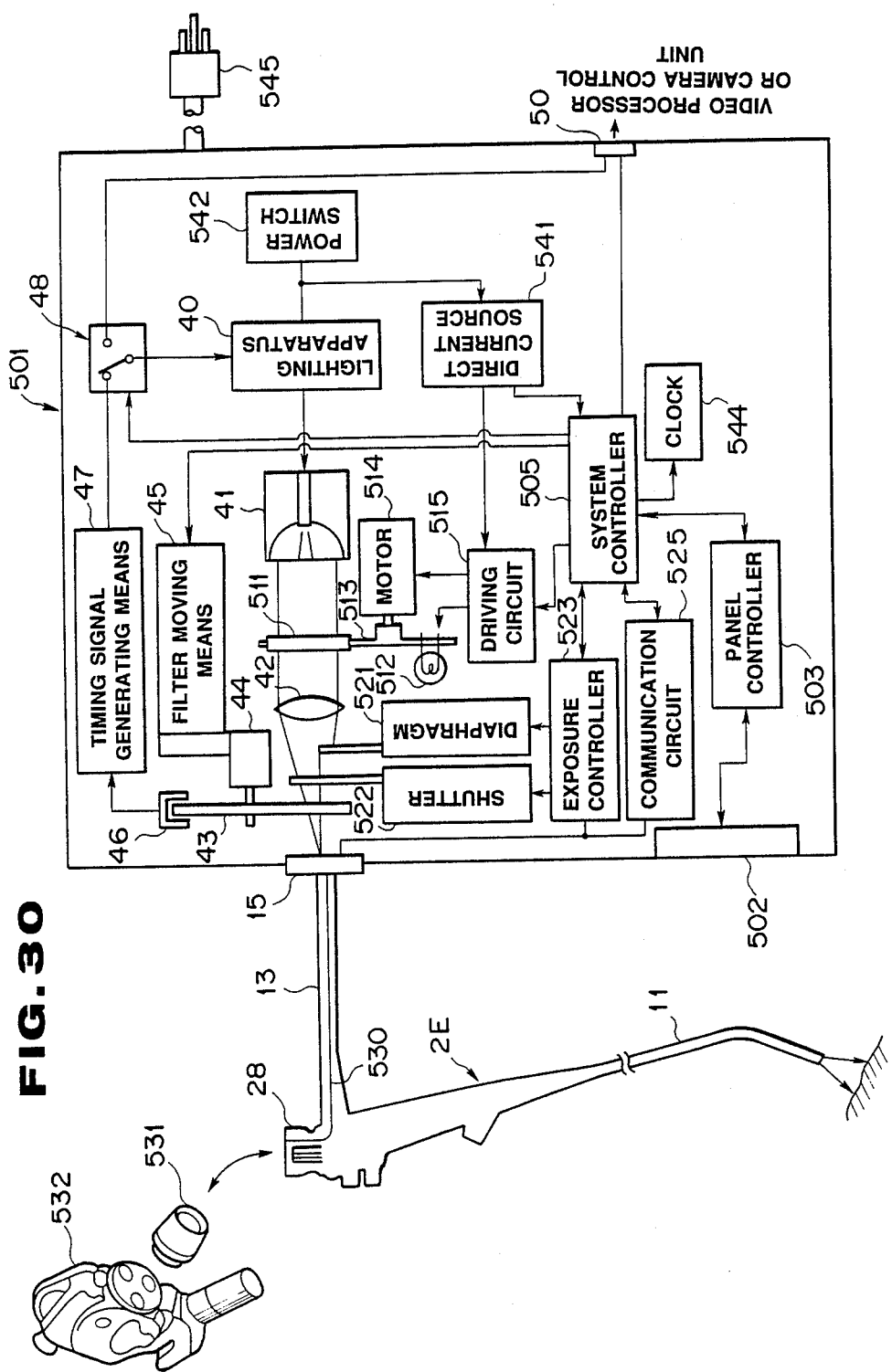
FIG. 30 is an explanatory view showing an endoscope light source apparatus of the eighth embodiment of the present invention.

The eighth embodiment of the present invention is shown in FIG. 30.

This embodiment is an endoscope light source apparatus 501 adapted particularly to the use of a cine camera and still camera.

The same as in the first embodiment, the endoscope light source apparatus 501 of this embodiment comprises a lighting apparatus 40, lamp 41, lens 42, color converting filter 43, motor 44, filter moving means 45, encoder 46, timing signal generating means 47, switching switch 48 and signal connector receptacle 50.

In this embodiment, a panel 502 making various displays and switch inputs is provided and is also the scope kind selecting means 49 in the first embodiment. The above mentioned panel 502 is connected to a system controller 505 controlling the entire light source apparatus 501 through a panel controller 503. This system controller 505 controls the above mentioned filter moving means 45 and switching switch 48.

A rotary frame 513 fitted with such filter 511 as an infrared ray cutting filter and an emergency lamp 512 is arranged between the lamp 41 and lens 42, can be rotated by a motor 514 and can selectively interpose one of the above mentioned filter 511 and emergency lamp 512 into the illuminating light path. The above mentioned emergency lamp 512 and motor 514 are driven by a driving circuit 515 which is controlled by the above mentioned system controller 505.

A diaphragm 521 and shutter 522 are provided between the above mentioned lens 42 and color converting filter 43 and are controlled by an exposure controller 523 which is controlled by the above mentioned system controller 505.

In this embodiment, a communication circuit 525 is provided and this communication circuit 525 and the above mentioned exposure controller 523 are connected to the light source connector receptacle 15.

In the fiber scope 2E adapted to use the light source apparatus 501 of this embodiment, the eyepiece part 28 and light source connector are provided with contacts connected with each other through a signal line 530. A cine camera 532 and a still camera not illustrated can be connected to the above mentioned eyepiece part 28, for example, through a cine camera adapter 531. An exposure detecting means and communication circuit are provided within the above mentioned cine camera 532 and still camera and are connected to the exposure controller 523 and communication circuit 525 within the light source apparatus 501 through the contacts and signal line 530 provided in the above mentioned fiber scope 2E. On the basis of the exposure information detected by the above mentioned exposure detecting means, the above mentioned controller 523 controls the diaphragm 524 and shutter 522. A communication is made between the communication circuit within the cine camera 532 or still camera and the communication circuit 525 within the light source apparatus 501 to make various controls.

By the way, a direct current power source 541 is connected to the system controller 505 and driving circuit 515 of the light source apparatus 501. A power switch 542 is connected to this direct current power source 541 and lighting apparatus 40. A clock 544 is connected to the above mentioned system controller 505. The light source apparatus 501 is provided with a power source plug 545.

By the way, in FIG. 30, only the fiber scope 2E and cine camera 532 are shown as endoscopes but it is needless to say that the other scopes 2A and 2B and television cameras 4A and 4B can be also used in the light source apparatus of this embodiment.

By the way, the above mentioned cine camera 532 requires a white color light as an illuminating light. As synchronized with the opening and closing of the shutter, the same as at the time of outputting a field sequential light, the light amount of the lamp 41 may be increased during the exposure period and may be decreased during the light interception period. Thereby, the light amount can be increased without substantially varying the power consumption and the power consumption can be reduced without varying the light amount.

The other formations, operations and effects are the same as in the first embodiment. In the case of using a continuously photographable motor driven camera as a still camera to be connected to the eyepiece part 28 of the fiber scope 2E, the same as in the case of the above mentioned cine camera, as synchronized with the opening and closing of the shutter, the light amount of the lamp 41 may be intermittently increased.

The other formations, operations and effects are the same as in the first embodiment.

By the way, in the eighth embodiment, at the time of outputting a field sequential light, the light amount may be increased to be larger than at the time of outputting a white color light by making the lamp current constant and without intermittently increasing the light amount.

By the way, the present invention is not limited to the above mentioned respective embodiments. For example, in the light source apparatus, as a means of switching a field sequential light and white color light, for example, the color converting filter may be provided with such white color light transmitting part as a hole besides the filters transmitting such field sequential lights as of R, G and B so that, when a field sequential light is to be output, a light intercepting plate or the like may cover the above mentioned white color light transmitting part by the centrifugal force of the rotary filter and, on the other hand, when a white color light is to be output, the color converting filter may be stopped in the position in which the light from the lamp passes through the above mentioned white color light transmitting part.

Also, at the time of outputting a field sequential light, the peak light amount will not be increased to be larger than at the time of outputting a white color light and, as synchronized with the exposure period of the field sequential type imaging means, the light amount will be intermittently increased so that the power consumption may be decreased without varying the light amount of the field sequential light.

The imaging means is not limited to a CCD but various solid state imaging devices can be used.

Both or one of the video processor 5 and camera control unit 6 may be made integral with the light source apparatus.

Also, the present invention can be applied not only to such flexible endoscope as the fiber scope 2E but also to a rigid endoscope.

As explained above, according to the present invention, a white color light and field sequential light can be output and, at the time of outputting a field sequential light, during the exposure period of the field sequential type imaging means, the light amount of the light source will be increased to be larger than outside the exposure period and, according to the second invention, a white color light and field sequential light can be output and, at the time of outputting a field sequential light, the light amount of the light source will be increased to be larger than at the time of outputting a white color light and therefore there is an effect that a sufficient light amount can be fed even at the time of outputting a field sequential light.

Also, according to the present invention, there is an effect that, at the time of outputting a field sequential light, the light emitted from the light source can be effectively utilized.

It is apparent that, in this invention, working modes different in a wide range can be formed on the basis of this invention without departing from the spirit and scope of the invention. This invention is not restricted by its specific working modes except being limited by the appended claims.

What is claimed is:

1. An endoscope light source apparatus which can feed an illuminating light to an endoscope requiring a white color light as an illuminating light and to an endoscope provided with a field sequential type imaging means and requiring as an illuminating light a field sequential light switched sequentially to lights in different wavelength ranges, comprising:

a light source emitting a white color light;

a light converting means interposed in the light path of the light emitted from said light source at least at the time of outputting a field sequential light and converting the white color light emitted from said light source to a field sequential light;

a selecting means selecting the kind of the emitted light from among a white color light and field sequential light; and a light amount controlling means whereby, when a field sequential light is selected by said selecting means, during the exposure period of said field sequential type imaging means, the light amount of said light source can be increased to be larger than outside the exposure period.

2. An endoscope light source apparatus which can feed an illuminating light to an endoscope requiring a white color light as an illuminating light and to an endoscope provided with a field sequential type imaging means and requiring as an illuminating light a field sequential light switched sequentially to lights in different wavelength ranges, comprising:

a light source emitting a white color light;

a light converting means interposed in the light path of the light emitted from said light source at least at the time of outputting a field sequential light and converting the white color light emitted from said light source to a field sequential light;

a selecting means selecting the kind of the emitted light from among a white color light and field sequential light; and a light amount controlling means whereby, when a field sequential light is selected, the light amount of said light source can be increased to be larger than at the time of outputting a white color light.

3. An endoscope light source apparatus according to claim 1 wherein, when a field sequential light is selected by said selecting means, during the exposure period of said field sequential type imaging means, said light amount controlling means can increase the light amount of said light source to be larger than outside the exposure period and at the time of outputting a white color light.

4. An endoscope light source apparatus according to any one of claims 1 to 3 wherein the endoscope provided with said field sequential type imaging means is an electronic endoscope having said field sequential type imaging means within the endoscope body.

5. An endoscope light source apparatus according to any one of claims 1 to 3 wherein said endoscope provided with a field sequential type imaging means comprises an endoscope body having an image transmitting means transmitting an object image from the tip part of the insertable part to the eyepiece part and a television camera removably connected to said eyepiece part and having said field sequential type imaging means.

6. An endoscope light source apparatus according to any one of claims 1 to 3 wherein said endoscope requiring a white color light as an illuminating light is a naked eye observable endoscope having an image transmitting means transmitting an object image from the tip part of the insertable part to the eyepiece part.

7. An endoscope light apparatus according to any one of claims 1 to 3 wherein said endoscope requiring a white color light as an illuminating light comprises an endoscope body having an image transmitting means transmitting an object image from the tip part of the insertable part to the eyepiece part and a television camera removably connected to said eyepiece part and having a simultaneous type imaging means.

8. An endoscope light source apparatus according to any one of claims 1 to 3 wherein said endoscope requiring a white color light as an illuminating light is an electronic endoscope having a simultaneous type imaging means within the endoscope body.

9. An endoscope light source apparatus according to any one of claims 1 to 3 wherein said endoscope requiring a white color light as an illuminating light comprises an endoscope body having an image transmitting means transmitting an object image from the tip part of the insertable part to the eyepiece part and a cine camera removably connected to said eyepiece part.

10. An endoscope light source apparatus according to any one of claims 1 to 3 further comprising a discriminating means discriminating the kind of the endoscope to be used, said selecting means selecting the kind of the light adapted to the endoscope to be used on the basis of the discriminating information of said discriminating means.

11. An endoscope light source apparatus according to claim 10 wherein said endoscope requiring a white color light as an illuminating light has a simultaneous type imaging means and said discriminating means senses whether a signal processing apparatus for said field sequential type imaging means or a signal processing apparatus for said simultaneous type imaging means is connected to said endoscope light source apparatus and discriminates the kind of the endoscope to be used.

12. An endoscope light source apparatus according to any one of claims 1 to 3 wherein said field sequential type imaging means is a solid state imaging device having exposure periods and charge transfer periods during the operation.

13. An endoscope light source apparatus according to any one of claims 1 to 3 wherein said light amount controlling means controls the current fed to said light source.

14. An endoscope light source apparatus according to claim 1 or 3 wherein said converting means is a rotary filter in which a plurality of filters transmitting lights in respectively different wavelength ranges are arranged in the peripheral direction and are sequentially interposed into the light path of the light emitted from said light source.

15. An endoscope light source apparatus according to claim 14 wherein said rotary filter has light intercepting parts between said respective filters and the periods in which said respective filters are interposed in the light path of the light emitted from said light source correspond to the exposure periods of said field sequential type imaging means.

16. An endoscope light source apparatus according to claim 14 wherein said rotary filter has no light intercepting part between said respective filters and, during the other periods than the exposure periods of said field sequential type imaging means, the boundaries of said respective filters are interposed in the light path of the light emitted from said light source.

17. An endoscope light source apparatus according to claim 14 wherein said light amount controlling means controls the light amount as synchronized with the rotation of said rotary filter.

18. An endoscope light source apparatus according to claim 2 wherein said converting means is a rotary filter in which a plurality of filters transmitting lights in respectively different wavelength ranges are arranged in the peripheral direction and are sequentially interposed into the light path of the light emitted from said light source.

19. An endoscope light source apparatus according to any one of claims 1 to 3 wherein saud converting means is a rotary filter in which a plurality of filters transmitting lights in respectively different wavelength ranges are arranged in the peripheral direction and are sequentially interposed into the light path of the light emitted from said light source and said selecting means has a means removably inserting said rotary filter into the light path of the light emitted from said light source.

20. An endoscope light source apparatus according to any one of claims 1 to 3 wherein said converting means is a rotary filter which has white color light transmitting parts and in which a plurality of filters transmitting lights in respectively different wavelength ranges are arranged in the peripheral direction and are sequentially interposed into the light path of the light emitted from said light source and said selecting means switches said rotary filter to be rotated in the light path of the light emitted from said light source and to be stopped in the position in which said white color light transmitting part is interposed in the light path of the light emitted from said light source.

* * * * *

UNITED STATES PATENT AND TRADEMARK OFFICE
CERTIFICATE OF CORRECTION

PATENT NO. : 4,924,856

DATED : May 15, 1990

INVENTOR(S) : Toshiaki NOGUCHI

It is certified that error appears in the above-identified patent and that said Letters Patent is hereby corrected as shown below:

On the title page, Item [30], "63-057262" should read --1-57262--.

Signed and Sealed this

Eleventh Day of February, 1992

Attest:

HARRY F. MANBECK, JR.

*Attesting Officer*  *Commissioner of Patents and Trademarks*